US008906095B2

(12) United States Patent
Christensen et al.

(10) Patent No.: US 8,906,095 B2
(45) Date of Patent: Dec. 9, 2014

(54) SPINAL IMPLANT, INSTRUMENT FOR PREPARATION AND METHOD OF USE

(71) Applicants: Finn Bjarke Christensen, Silkeborg (DK); Bruce H. Robie, North Andover, MA (US); Peter J. Lauridsen, Risskov (DK)

(72) Inventors: Finn Bjarke Christensen, Silkeborg (DK); Bruce H. Robie, North Andover, MA (US); Peter J. Lauridsen, Risskov (DK)

(73) Assignee: FBC Device ApS, Risskov (DK)

( * ) Notice: Subject to any disclaimer, the term of this patent is extended or adjusted under 35 U.S.C. 154(b) by 0 days.

(21) Appl. No.: 14/023,601

(22) Filed: Sep. 11, 2013

(65) Prior Publication Data
US 2014/0336652 A1 Nov. 13, 2014

Related U.S. Application Data

(63) Continuation-in-part of application No. PCT/US2012/028158, filed on Mar. 8, 2012.

(60) Provisional application No. 61/451,840, filed on Mar. 11, 2011.

(51) Int. Cl.
*A61F 2/44* (2006.01)
*A61B 17/16* (2006.01)

(52) U.S. Cl.
CPC ........... *A61F 2/4465* (2013.01); *A61B 17/1671* (2013.01)
USPC ...................................................... 623/17.15

(58) Field of Classification Search
USPC .......................................... 623/17.11–17.16
See application file for complete search history.

(56) References Cited

U.S. PATENT DOCUMENTS

| 5,314,477 A | 5/1994 | Marnay |
| 5,507,816 A | 4/1996 | Bullivant |
| 5,556,431 A | 9/1996 | Buttner-Janz |
| 5,562,738 A | 10/1996 | Boyd et al. |
| 5,676,701 A | 10/1997 | Yuan et al. |
| 5,893,889 A | 4/1999 | Harrington |
| 5,895,428 A | 4/1999 | Berry |
| 5,899,941 A | 5/1999 | Nishijima et al. |
| 6,039,763 A * | 3/2000 | Shelokov ................... 623/17.16 |

(Continued)

OTHER PUBLICATIONS

PCT International Search Report and Written Opinion of dated Jul. 18, 2012 from PCT/US2012/028158 filed Mar. 8, 2012.

(Continued)

*Primary Examiner* — David Bates
(74) *Attorney, Agent, or Firm* — McCarter & English, LLP

(57) ABSTRACT

The present disclosure relates to the field of spine disc implants. Exemplary embodiments of the disclosed spinal disc implants advantageously and ultimately provide fusion with the body of the vertebra and stabilization of the spine in an anatomically correct position, e.g., in cervical, thoracic and/or lumbar regions. More particularly, the present disclosure is directed to a disc implant that addresses and overcomes the shortcomings of the prior implants by providing first and second inter-vertebral elements that are movably coupled relative to each other and are adapted to permit bone in-growth over time. Thus, the disclosed spinal disc implants permit relative movement between the first and second inter-vertebral elements upon implantation and after the patient is mobilized—thereby permitting the implant to assume a desired position based on the specific and unique spinal balance of the patient in an initial post-implantation period—but then the first and second inter-vertebral elements become fixed relative to each other (i.e., fused). The present disclosure also provides advantageous instrumentation and associated methods for positioning a spine disc implant in a desired anatomical location.

20 Claims, 8 Drawing Sheets

(56) References Cited

U.S. PATENT DOCUMENTS

| | | | |
|---|---|---|---|
| 6,231,609 B1 | 5/2001 | Mehdizadeh | |
| 6,368,350 B1 | 4/2002 | Erickson et al. | |
| 6,540,785 B1 * | 4/2003 | Gill et al. | 623/17.14 |
| 6,641,614 B1 | 11/2003 | Wagner et al. | |
| 6,770,095 B2 | 8/2004 | Grinberg et al. | |
| 6,893,465 B2 | 5/2005 | Huang | |
| 6,902,566 B2 | 6/2005 | Zucherman et al. | |
| 6,986,789 B2 | 1/2006 | Schultz et al. | |
| 7,182,784 B2 | 2/2007 | Evans et al. | |
| 7,198,644 B2 | 4/2007 | Schultz et al. | |
| 7,320,688 B2 | 1/2008 | Foley et al. | |
| 7,326,250 B2 | 2/2008 | Beaurain et al. | |
| 7,331,994 B2 | 2/2008 | Gordon et al. | |
| RE40,260 E | 4/2008 | Buhler | |
| 7,491,241 B2 | 2/2009 | Errico et al. | |
| 7,537,615 B2 | 5/2009 | Lemaire | |
| 7,550,009 B2 | 6/2009 | Arnin et al. | |
| 7,553,320 B2 | 6/2009 | Molz, IV et al. | |
| 7,582,115 B2 | 9/2009 | Weber | |
| 7,585,325 B2 | 9/2009 | Schneid et al. | |
| 7,771,481 B2 | 8/2010 | Khandkar et al. | |
| 7,780,676 B2 | 8/2010 | Lakin | |
| 7,794,465 B2 | 9/2010 | Marik et al. | |
| 7,842,088 B2 | 11/2010 | Rashbaum et al. | |
| 7,887,589 B2 | 2/2011 | Glenn et al. | |
| 7,892,262 B2 | 2/2011 | Rhoda et al. | |
| 7,918,889 B2 | 4/2011 | Vittur et al. | |
| 7,927,374 B2 | 4/2011 | Duggal et al. | |
| 7,959,678 B2 | 6/2011 | Filippi et al. | |
| 7,963,994 B2 | 6/2011 | Biedermann et al. | |
| 8,007,536 B2 | 8/2011 | Christensen | |
| 8,016,885 B2 | 9/2011 | Khalili | |
| 8,038,716 B2 * | 10/2011 | Duggal et al. | 623/17.14 |
| 8,057,547 B2 | 11/2011 | Hurlbert et al. | |
| 8,070,814 B2 | 12/2011 | Zubok et al. | |
| 8,075,596 B2 | 12/2011 | Molz | |
| 8,097,035 B2 | 1/2012 | Glenn et al. | |
| 8,133,281 B2 | 3/2012 | Lechmann et al. | |
| 8,147,552 B2 | 4/2012 | Ralph et al. | |
| 8,202,320 B2 | 6/2012 | Burgess et al. | |
| 8,211,178 B2 | 7/2012 | Melkent et al. | |
| 8,252,058 B2 | 8/2012 | Bernero | |
| 8,257,441 B2 | 9/2012 | Duplessis et al. | |
| 8,303,660 B1 | 11/2012 | Abdou | |
| 8,303,661 B2 | 11/2012 | Keller | |
| 8,323,342 B2 | 12/2012 | Schwab | |
| 8,349,017 B2 | 1/2013 | Marnay et al. | |
| 8,403,989 B2 | 3/2013 | Buettner-Janz et al. | |
| 8,454,699 B2 | 6/2013 | Duggal et al. | |
| 8,496,707 B2 | 7/2013 | Adamo | |
| 8,506,631 B2 | 8/2013 | De Villiers et al. | |
| 8,506,634 B2 | 8/2013 | Marnay et al. | |
| 8,556,973 B2 | 10/2013 | Kwak et al. | |
| 8,585,764 B2 | 11/2013 | Copf, Jr. | |
| 8,597,358 B2 | 12/2013 | Landry et al. | |
| 8,632,594 B2 | 1/2014 | Williams et al. | |
| 8,636,804 B2 | 1/2014 | Errico | |
| 8,702,797 B2 | 4/2014 | Lechmann | |
| 2005/0197706 A1 | 9/2005 | Hovorka et al. | |
| 2006/0224241 A1 * | 10/2006 | Butler et al. | 623/17.15 |
| 2006/0241769 A1 * | 10/2006 | Gordon et al. | 623/17.13 |
| 2009/0082867 A1 | 3/2009 | Sebastian Bueno et al. | |
| 2011/0087331 A1 | 4/2011 | Reichen et al. | |
| 2012/0123545 A1 * | 5/2012 | Khandkar et al. | 623/17.16 |
| 2012/0136443 A1 * | 5/2012 | Wenzel | 623/17.14 |
| 2012/0245688 A1 * | 9/2012 | Vanaclocha Vanaclocha | 623/17.16 |
| 2012/0323332 A1 * | 12/2012 | Ferree et al. | 623/17.16 |
| 2013/0110240 A1 * | 5/2013 | Hansell et al. | 623/17.16 |
| 2013/0131813 A1 * | 5/2013 | Ferree et al. | 623/17.16 |
| 2013/0226299 A1 | 8/2013 | Zubok et al. | |

OTHER PUBLICATIONS

Serial No. PCT/US2012/0128158, Filing Date Mar. 8, 2012, Publication No. WO 2012/125382 Sep. 20, 2012.

* cited by examiner

SPINAL IMPLANT, INSTRUMENT FOR PREPARATION AND METHOD OF USE

CROSS-REFERENCE TO RELATED APPLICATION

The present application is a non-provisional application that claims priority benefit to (i) a PCT application entitled "Spinal Implant, Instrument for Preparation and Method of Use," which was filed with the U.S. Receiving Office on Mar. 8, 2012, and assigned Serial No. PCT/US2012/128158, and (ii) a provisional patent application entitled "Spinal Implant, Instrument for Preparation and Method of Use," which was filed with the U.S. Patent and Trademark Office on Mar. 11, 2011, and assigned Ser. No. 61/451,840. The entire contents of the foregoing patent applications are incorporated herein by reference.

BACKGROUND

1. Technical Field

The present disclosure relates to the field of vertebral disc implants, i.e., disc implants having applicability throughout the vertebral column. Exemplary embodiments of the disclosed vertebral disc implants advantageously and ultimately provide fusion with the body of the vertebra and stabilization of the spine (e.g., cervical, thoracic and/or lumbar spinal regions) in an anatomically correct position. More particularly, the present disclosure is directed to a disc implant that addresses and overcomes the shortcomings of the prior implants by providing first and second inter-vertebral elements that are movably coupled relative to each other and are adapted to permit bone in-growth over time. Thus, the disclosed spinal disc implants permit relative movement between the first and second inter-vertebral elements upon implantation and after the patient is mobilized—thereby permitting the implant to assume a desired position based on the specific and unique spinal balance of the patient in an initial post-implantation period—but then the first and second inter-vertebral elements become fixed relative to each other (i.e., fused). The present disclosure also provides advantageous instrumentation and associated methods for positioning a spine disc implant in a desired anatomical location.

2. Background Art

Back pain with or without leg pain is a major problem in the adult population. The pain may have multiple causes and in certain instances, surgery may be required to mitigate such pain. Lower back pain may be caused by displacement of vertebrate bodies and/or intermediate discs in the lumbar region of the spine. The L4-L5 and L5-S1 regions of the spine are particularly vulnerable. For patients with severe pain that doesn't respond to conservative treatment, fusion surgery is currently viewed as a viable option. Spinal fusion surgery (fusing one vertebra to another) is often performed to decrease motion at a painful motion segment, thereby reducing associated pain at that segment. This abnormal and painful motion phenomenon can be caused by disc-related issues (e.g., discogenic pain and/or degenerative disc disease), abnormal slippage and motion of the vertebra (e.g., spondylolisthesis and/or spondylolysis), or other degenerative spinal conditions, including but not limited to facet joint degeneration. In addition, a spine fusion may be indicated for any condition that causes excessive instability of the spine, such as certain fractures, infections, tumors and/or spinal deformity (such as scoliosis).

Interbody surgeries may be performed either from the front or from the back of the patient and exemplary procedures are described as "posterior lumbar interbody fusion" (PLIF), "transforaminal lumbar interbody fusion" (TLIF), "lateral lumbar interbody fusion" (XLIF), "anterior interbody fusion" (AIF), "anterior lumbar interbody fusion" (ALIF) and "anterior cervical discectomy and fusion" (ACDF). As a group, the noted fusion procedures are generally referred to as "circumferential fusion." Each of the noted circumferential fusion procedures generally involves removing a disc from between two adjacent vertebrae and inserting a structure, e.g., bone, into the space created between the two vertebral bodies. During conventional posterolateral spine fusion (PLF) surgery, a graft is generally laid out in the posterolateral portion of the spine. Posterior surgery has been shown to yield acceptable clinical results and is claimed to further improve outcome by adding anterior column support. However, posterior surgery procedures are unfortunately associated with a long recovery compared to exclusively anterior surgery.

In general, the position of the disc implant is determined during surgery. The position is influenced by factors such as the manner of fixation employed by the surgeon and/or by the design of the implant used. As the fusion requires stabilization until bone growth has occurred, which may often take several months (e.g., 3-6 months), the position is important to achieving a fusion. If the position is not correct, the surgery may result in a non-union (a failure to achieve fusion) or may even result in secondary effects caused by stress placed on the neighboring discs. If necessary, subsequent surgeries are complicated by the previous surgery.

Three general types of "total disc replacement" (TDR) implants are known. A first TDR implant may be characterized as an unconstrained design and such design appears to have some advantages as unconstrained designs are more likely to provide a physiologic mobile instantaneous axis of rotation (IAR), thus displaying a greater range of motion in vivo. The lack of constraint in such unconstrained designs may prevent excessive facet joint or capsuloligamentous loads in the extremes of flexion and extension. Furthermore, since the IAR is mobile, the unconstrained designs may be less sensitive to small errors in implant placement, for example, the Charite total disc replacement. A second TDR implant may be characterized as a constrained design and constrained devices appear to have an advantage in protection of the posterior elements from shear loading, for example the FLEXICORE implant (Stryker Spine, Allendale, N.J.). Spinal shear loads of considerable magnitude occur during activities of daily living. A third group of TDR implants may be characterized as semi constrained implants and include commercially available products such as the PRODISC implant (Synthes Spine, West Chester, Pa.).

The patent literature reflects efforts to address issues related to back and/or leg pain and/or spinal instabilities. Thus, for example, U.S. Patent Publication No. 2006/0235529 to Ralph et al. (the "Ralph '529 publication") is directed to a disc implant that is expressly designed to ensure that fusion does not occur. The Ralph implant features opposed first and second plates that are movably coupled relative to each other. Exemplary embodiments of the Ralph '529 publication include a "spider spring" that exhibits "long cycle life to mimic the axial biomechanical performance of the normal human intervertebral disc." [Ralph '529 publication, para. 0030] The exterior surfaces of the Ralph implant include a convex mesh and a porous ring that facilitate bone in-growth so as to anatomically fix the implant, i.e., "permanently securing the prosthesis within the invertebral space." [Ralph '529 publication; para. 0019] Thus, the Ralph '529 publication contemplates bone in-growth to fix the first plate relative to a first vertebral body and bone in-growth to fix the second plate relative to a second vertebral body, while maintaining relative motion between the first and second plates. The Ralph '529 publication is thus clearly designed to ensure that bone in-growth between the first and second plates is avoided. The Ralph '529 publication explicitly identifies conventional fusion cage technology as inferior because, according to Ralph et al., bone fusion is both undesirable and detrimental to patients.

U.S. Pat. No. 6,641,614 to Wagner et al. (the "Wagner '614 patent") provides a fusion device that includes a pair of engaging plates and an alignment device positioned therebetween. The alignment device is adapted to adjust the height between the engaging plates, thereby permitting customization of the fusion device to a particular patient. Of note, the height of the Wagner fusion device is generally adapted to differ from anterior end to posterior end. The alignment device of the Wagner '614 patent necessarily relies on the surgeon's judgment in arriving at an "adjusted" relative position between the engaging plates. In exercising such judgment, the surgeon is required to interact with the adjustment device using specialized instrumentation. Thus, the "adjustability" enabled by the Wagner fusion device is, at best, dependent on a surgeon's clinical experience in arriving at an "adjusted" height between engaging plates that may—or may not—be advantageous for the specific patient. Indeed, method(s) for reliably selecting the correct spinal position on an individual basis at the time of surgery is/are not currently available.

As with conventional fusion devices, the engaging plates of the Wagner '614 patent include "a plurality of openings to allow bone growth to occur through the engaging plates," e.g., openings having a total area of about 60% to 80% of the total surface area of the engaging plates. [Wagner '614 patent, col. 2, lines 37-42] Once implanted and height-adjusted, the Wagner fusion device is fixed in position relative to the adjacent vertebrae. Thus, unlike the disc implant of the Ralph '529 publication, the Wagner fusion device is not adapted and/or intended "to mimic the functionality of a healthy natural invertebral disc." [Ralph '529 publication, para. 0118]

Thus, as the Ralph '529 publication and the Wagner '614 patent illustrate, the teachings in the patent literature have generally fallen into two (2) distinct categories: a first category represented by the Ralph '529 publication that are designed to ensure continued relative movement between opposed plates post-implantation, and a second category represented by the Wagner '614 patent that are designed to effectuate prompt fusion between adjacent vertebrae post-implantation.

Against this backdrop, an innovative approach to spinal stabilization is disclosed in U.S. Pat. No. 8,007,536 to Christensen which discloses a disc implant that includes two intervertebral elements which are flexibly connected via coupling means. Following surgery, the relative movability of the two inter-vertebral elements is decreased overtime, as bone in-growth occurring around the implant and specifically through osseointegrative sections gradually decrease the movability of the elements relative to each other. Following bone in-growth, the relative movability of the implant elements is replaced by relative fixation of the elements. The fixation of the spinal implant advantageously occurs in a position affected by the movement of the patient and the loading in the patient's spine, and is thereby more acceptable to the patient. The entire content of the Christensen '536 patent is incorporated herein by reference.

A goal of the present disclosure is to further improve the previous work of Christensen in enabling fixation of a spinal region, e.g., cervical, thoracic and/or lumbar spinal region, in a position affected by the movement of the patient and the loading in the patient's spine. In addition, the present disclosure provides instrumentation and implant(s) that permit/facilitate placement of an implant in a desired orientation/position, e.g., through cooperative features. These and other needs are satisfied by the spinal implants disclosed herein.

SUMMARY

The present disclosure provides a disc implant for use in spine surgery and methods of spine surgery wherein said disc implant is used. The disclosed disc implants have wide ranging clinical application, e.g., in the cervical, thoracic and/or lumbar regions of the spine. The disclosed disc implants generally include a pair of opposed elements that are initially free to move relative to each other, but that become fixed relative to each other over time. Thus, the opposed elements demonstrate an initial relative motion post-implantation that is lost over time by bone in-growth which ultimately leads to fixation of the opposed disc elements relative to each other, i.e., fusion.

The spinal disc implants of the present disclosure are believed to address issues that have led to a lack of success in prior surgical procedures which may be attributed to fusion/fixation of implants in a sub-optimal position. Sub-optimal positioning of prior art implants may be due to the fact that the position of fusion/fixation is determined during surgery where the back is in a position different from the position employed during the awake hours when the patient is predominantly in a standing/loaded or seated position.

The disclosed spinal disc implants overcome the foregoing limitations of prior art surgical implants by advantageously allowing relative motion of the elements of the disc implant for a period of time post-implantation. More particularly, the disclosed spinal disc implants include opposed elements that are movably coupled to each other for a period of time following surgical implant, but such opposed elements assume a fixed position relative to each other after a period of time post-implantation based on bone growth that serves to fix the elements in a desired relative position. Of note, the final fixed position of the opposed elements is not determined by the surgeon during implantation, but instead is uniquely determined by anatomical factors associated with the patient and spinal movement experienced by the patient post-implantation. The period of post-implantation movability between the opposed elements advantageously allows the ultimate fixation due to bone in-growth to occur in a position affected by the unique loads/motions of the patient, thereby ensuring that the position of fixation will be closer to the natural position of the patient and increasing the likelihood of a successful recovery, enhanced spinal stability and/or reduction in back and/or leg pain and adjacent disc disease.

Thus, the present disclosure relates to implants to provide adjustable interbody fusion of a spinal motion segment (e.g., cervical, thoracic and/or lumbar segment) as well as implants for an artificial disc, instruments to prepare the bone adjacent to the implants, and associated features on the implant and methods of use of the instruments and implants.

An objective of the present disclosure is to enable certain motions after surgery so that the patient, due to anatomy, muscle forces and more generally posture and spinal balance, may determine an appropriate position for spinal fusion. While allowing motions, the apparatus and associated methods of the present disclosure advantageously provide certain limits on motions and also provide resistive forces to certain other motions.

Another objective of the present disclosure is to provide a spine implant characterized by an overall shape that enables placement of significant amounts of bone graft, bone substitute(s) and/or bone graft extender(s) anteriorly to the spine implant in connection with implantation thereof as a way to maximize the fusion mass, including means to connect or otherwise associate the bone materials to the implant.

A further objective of the present disclosure is to provide articulating geometry for a two piece artificial disc that has the capability to accommodate unconstrained (or substantially unconstrained) motion in flexion/extension, lateral bending and axial rotation. However, while allowing such unconstrained/substantially unconstrained motions, the disclosed spine disc provides certain limits on certain other motions and/or provides resistive forces to certain other motions.

Still another objective of the present disclosure is to describe instrument(s) to form a cavity in the bone adjacent to the desired position of the implant, implant features to fit within the cavity and methods of use of the instruments and implants. In particular, the present disclosure advantageously provides resistance to relative motion between the implant and bone, especially anterior motion of the implant relative to the bone.

In exemplary embodiments of the present disclosure, the disclosed disc implant may function as a fusion implant device or an artificial disc device. The disclosed implant generally includes a first inter-vertebral element defining a first inner face and a first outer face and a second inter-vertebral element defining a second inner face and a second inner face. The first inner face and the second inner face of the respective inter-vertebral elements typically include structural features that define an articulating geometry. The articulating geometry accommodates relative motion between the first and second inter-vertebral elements, e.g., such articulating geometry being characterized at least in part by medial-lateral and anterior-posterior profiles that are not the same. At least one of the medial-lateral and anterior-posterior profiles of the first and second inter-vertebral elements may be substantially the same in at least one direction. In addition, the first and second inter-vertebral elements may include one or more structural features that resist, but do not prevent, axial rotation and anterior-posterior translation.

The first and second inter-vertebral elements of the disclosed implant may also include one or more structural features that limit lateral bending.

At least one fusion block may be provided for association with at least one of the first and second inter-vertebral elements. The fusion block(s) may be mounted with respect to the first and/or second inter-vertebral element. The fusion block(s) are generally positioned anterior to the first and second inter-vertebral elements. In addition, the fusion block(s) generally include a body and a connector stem that is adapted to be mounted with respect to a hole formed in one of the first and second inter-vertebral elements.

Exemplary disc implants according to the present disclosure include first and second inter-vertebral elements that each define a central region, a first wing that extends laterally relative to the central region in a first direction, and a second wing that extends laterally in a second direction relative to the central region. The central region of the first inter-vertebral element and the central region of the second inter-vertebral element are generally adapted to be placed in abutting relation and the abutting engagement of such central regions establishes at least in part the articulating geometry thereof.

Cooperative structures are typically defined on the respective wings of the first and second inter-vertebral elements. The cooperative structures advantageously accommodate relative motion between the first and second inter-vertebral elements. In an exemplary implantation of the present disclosure, the cooperative structures include upstanding bosses and slots. Each cooperative upstanding boss and slot typically defines an anterior gap, a posterior gap and a distal gap.

The wings of the first and second inter-vertebral elements may define openings that accommodate bone in-growth. Thus, the first and second inter-vertebral elements may be movably coupled relative to each other upon initial implantation, and may become fixed or fused relative to each other after a period of time post-implantation. Fixation or fusion is generally accomplished due to bone in-growth, e.g., through openings formed in the first and second inter-vertebral elements and/or anterior to the first and second inter-vertebral elements. In addition, the outer surface of the first and/or second inter-vertebral elements may include surface features that promote fixation relative to adjacent anatomical structures, e.g., barbs, pyramidal elements, coatings and combinations thereof. The first and second intervertebral elements may also include a plurality of anteriorly directed openings along edge(s) thereof, such plurality of openings functioning to accommodate at least one of (i) mounting of fusion block(s), and (ii) interaction with an instrument for clinical placement thereof.

The first and second inter-vertebral elements are generally movably coupled so as to define a center of rotation that is automatically repositionable post-implantation. In exemplary embodiments, the contact point or contact region between the two inter-vertebral elements may be automatically repositionable within a zone or region that includes both shifts in anterior-posterior and medial-lateral directions, and based on the curvatures of the elements, in the superior-inferior direction. It is also to be understood that by the movement of the contact point/region and relative positions and orientations of the two inter-vertebral elements, the center of rotation of the two components is also shifted three dimensionally (anterior-posterior, medial-lateral, and superior-inferior).

The present disclosure further provides surgical instrument(s) that include (i) a shaft, (ii) an operating tool positioned on the shaft, and (iii) a trial implant defining a cavity within which the operating tool is positioned. The trial implant is generally configured and dimensioned to fit in a disc space. In addition, the operating tool is typically adapted to create a cavity in two adjacent bone structures. The operating tool is also generally adapted to be moved between at least two positions, at least one of such positions positioning at least a portion of the operating tool extends outward from the trial implant. The trial implant may define openings on a first and on a second side thereof, and the operating tool may be adapted to move into an operative position extending at least in part through the first and second openings. A boss may be defined at a distal end of the shaft and a cooperating hole may be defined in the trial implant for receipt of the boss.

The present disclosure further provides a spinal implant that defines a raised feature for cooperation with a cavity defined in a bone structure to prevent anterior motion of the implant.

In exemplary methods associated with the present disclosure, the method includes the steps of:
positioning an operative portion of a surgical instrument into a disc space, the surgical instrument including an elongated shaft and at least one bone cutting element;
rotating the shaft of the bone cutting instrument to activate the at least one bone cutting element to create a cavity in the endplate of a bone;

removing the operative portion of the surgical instrument from the disc space; and inserting an implant with a raised feature to mate with the cavity created by the at least one bone cutting element.

In addition, the disclosed method may include (i) positioning the operative portion of the surgical instrument in the disc space with the at least one bone cutting element in a closed or shielded position, and (ii) moving the at least one bone cutting element from the closed or shielded position to an open or operative position within the disc space. The bone cutting element of the bone cutting instrument may be adapted to be operative on both sides of a trial implant within the disc space. The bone material harvested from the vertebral endplates can be collected and used for analytical purposes, e.g., biopsy, and/or to facilitate bone grafting operations. In exemplary embodiments of the present disclosure, an instrument and/or instrument accessory may be provided to capture and retain the harvested bone, e.g., bone shavings generated when creating a desired cavity for implant insertion.

Additional features, functions and benefits of the disclosed spinal disc implants will be apparent from the description which follows, particularly when read in conjunction with the appended figures.

BRIEF DESCRIPTION OF DRAWINGS

To assist those of skill in the art in making and using the disclosed spinal disc implants, reference is made to the accompanying figures, wherein.

DESCRIPTION OF EXEMPLARY EMBODIMENT(S)

Figure 1:
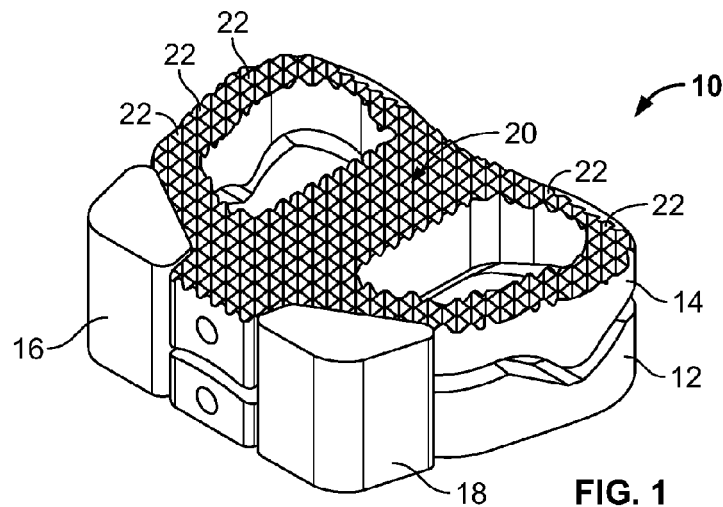
FIG. 1 is an isometric view of an exemplary implant according to the present disclosure.

The present disclosure is directed to spinal disc implants for use in spinal procedures, e.g., cervical, thoracic and/or lumbar procedures. The disclosed spinal disc implants are advantageously capable of stabilizing the spine and addressing related spinal issues. The disclosed disc implant stimulates fusion with neighboring vertebrate bodies and, based on the design and operation of the disclosed disc implant, facilitates fixation over time of the disc implant in a physiological position. Thus, in exemplary embodiments of the present disclosure, the disc implant may be used for insertion in the lumbar, thoracic and/or cervical spine region(s).

1. Disc Implant

Exemplary disc implants according to the present disclosure are adapted for clinical insertion between vertebrate bodies. The implant generally comprises two elements, which are coupled together forming the disc implant. The top and bottom surface of the implant, when viewed as positioned in a standing individual, are referred to as first and second outer fusion surfaces. The opposing surfaces of the two elements are described as internal coupling surfaces and include features/cooperative mechanisms that advantageously function to movably couple the elements relative to each other upon initial implantation of the disclosed spinal implant. Thus, the coupling means/mechanism serves to connect and/or align the first and second inter vertebral elements relative to each other. The coupling of the inter-vertebral elements regulates the movement of said first and second inter-vertebral elements relative to each other, i.e., prior to fixation of the first and second inter-vertebral elements relative to each other based on bone in-growth. Thus, coupling of said two inter-vertebral elements does not fixedly position the elements relative to each other. Minor movements of the elements relative to each other in at least one direction are generally permitted when said elements are coupled according to the present disclosure.

A third element may be advantageously positioned between the first and second elements described herein. Thus, for example, a non-metal component may be positioned between the first and second elements so as to be positioned between contact regions thereof. The non-metal component may be fabricated from a polymeric material, e.g., polyethylene, polyether ketone ketone (PEKK) and/or polyether ether ketone (PEEK). The non-metal component may take the form of a sheet, relatively thin block or surface treatment, and advantageously functions to prevent metal-to-metal contact, thereby reducing the potential for metal failure. Indeed, a sheet and/or block of the disclosed polymeric material may function as a wedge-like structure when introduced between the first and second elements in situ. In exemplary embodiments, the disclosed polymeric material may be positioned and/or applied to the "male" portion(s) of the first and/or second elements of the disclosed inter-vertebral elements.

Each of the first and second inter-vertebral elements may be stabilized to the adjacent vertebra after insertion by suitable means, e.g., one or more barbed extensions, until fusion of the disclosed spinal implant with adjacent vertebra is obtained/achieved. Thus, fusion/fixation of an implant with neighboring/adjacent bones—both for the disclosed spinal implants and conventional spinal implants—occurs at the outer surface(s) of the disc implant.

For purposes of the present disclosure, a "fixed implant" describes or references an implant wherein the inter-vertebral elements of said implant are not movable relative to each other, i.e., the first and second inter-vertebral elements are substantially fixed relative to each other based on bone in-growth that overrides the initial movable coupling that exists between the first and second inter-vertebral elements. By contrast, fusion of an implant with neighboring vertebra occurs at the outer surface(s) of the disc implant.

As described herein below, the disclosed spinal implants advantageously benefit from the temporal nature of the movability of the first and second inter-vertebral elements relative to each other that is achieved clinically based on the structural design and operation of the disclosed disc implant. Thus, first and second inter-vertebral elements of the disclosed implant remain relatively movable for a first period of time post-implantation, e.g., at least one (1) day after insertion, and then the first and second inter-vertebral elements become substantially fixed relative to each other after such first period of time, thereby converting the disclosed spinal implant to a fixed implant, e.g., less than twelve (12) to eighteen (18) months after insertion.

Thus, exemplary disc implants of the present disclosure include a first inter-vertebral element having a first outer fusion surface and a first internal coupling surface, a second inter-vertebral element having a second outer fusion surface and a second internal coupling surface, a coupling means/mechanism for movably connecting/coupling the first and second inter vertebral elements relative to each other. In addition, each inter-vertebral element generally includes one or more osseointegrative sections enabling/facilitating fixation of the first and second elements relative to each other over time, wherein the first and second elements of the implant remains relatively movable for at least one (1) day after insertion and the implant is converted into a fixed implant less than twelve (12) to eighteen (18) months after clinical insertion/implantation.

Spinal disc implants of the present disclosure are described in greater detail with the reference to the accompanying figures herein below. However, before addressing such exemplary implementations, the present disclosure provides overview information related to the shape, coupling means/mechanisms, size, material, coating, coating material, osseointegrative section(s)/openings, incisions/circumferential inset regions, temporal movability and methods of treatment associated with the advantageous spinal disc implants disclosed herein.

a. Shape

The disc implant according to the invention may have any shape that enables transient stabilization and stimulates long term fixation by fusion and bone in-growth.

The shape of the disc implant, as seen from the top, may include geometries such as a round, circular, oval, oblate or kidney shape. The disc implant may be designed for use in posterior or anterior surgery, but is preferably designed for use in anterior surgery, which may lead to a shorter recovery period after surgery. Alternatively, the disclosed implant may be designed for transforaminal lumbar interbody fusion or lateral lumbar interbody fusion.

b. Coupling Means/Mechanisms

The coupling means/mechanism of the first and second inter-vertebral elements should allow minor movements of the first and second inter-vertebral elements relative to each other, e.g., during the initial period post-implantation. The coupling means/mechanism is preferably located on the internal coupling surfaces of the first and second inter-vertebral elements. The area/volume formed by the internal coupling surface of the inter-vertebral elements may be referred to as the coupling zone of the implant. In order to obtain temporal movability of the disc implant, coupling of the first and second inter-vertebral elements does not result in formation of a rigid implant. As noted above, a non-metal component, e.g., a polymeric sheet, block and/or surface treatment, may be positioned between the coupling means/mechanism, thereby limiting the metal-to-metal contact therebetween. As illustrated in the figures presented herein, the exemplary couplings of the internal surfaces leaves some room for movement of the first and second elements relative to each other in at least one direction.

c. Size

The circumference of the disc implant may be smaller than the circumference of the corpus. In particular, the geometry of the disclosed spinal disc implant may be defined such that the basis of the corpus protrudes relative to the implant at the front thereof. For example, the corpus may protrude at least 0.2 mm relative to the implant, and optionally by as much as 0.4 mm or 0.6 mm past the edge of the implant. In further exemplary embodiments of the present disclosure, the distance from the outer edge of the implant to the edge of the corpus is defined such that the distance is on the order of 5 mm or greater.

Such dimensional arrangement may advantageously provide and/or permit stimulation of bone growth at or along the side of the disc implant and, following fixation of the inter-vertebral elements relative to adjacent vertebral bodies, bone tissue may join at or along the outer edges of the disclosed inter-vertebral elements, thereby further fixing the inter-vertebral elements relative to each other after a period of time post-implantation.

d. Material

The disc implants according to the present invention may be fabricated from any material(s) suitable for implantation. Thus, the disclosed implant may be constructed from one or more materials selected from, but not limited to, the group of ceramics, polymers, bone and metals. Preferred are metals. polymers and ceramics. The material(s) may be in states of glassy, rubbery, semi-crystalline, or crystalline, before and/or after processing into the implant.

In exemplary embodiments of the present disclosure, the disclosed spinal implants may be constructed of metal or metal alloys selected from the group of, but not limited to, stainless steel, cobalt-chromium, titanium (Ti), titanium alloys, shape memory alloys, e.g., NiTi, tantalum (Ta), niobium (Nb), zirconium (Zr) and platinum (Pt). Preferred metals and metal alloys are titanium, tantalum, titanium alloys, and cobalt-chromium and alloys thereof. Exemplary cobalt-chromium materials for use according to the present disclosure include CoCrMo alloys. Exemplary titanium alloys for use according to the present disclosure include Ti6Al4V. Exemplary stainless steel materials for use according to the present disclosure include austenitic stainless steels, especially types 316 and 316L, and Ni-free stainless steel.

Metals, such as transition metals, may be used to fabricate disc implants according to the present disclosure. For example, tantalum (Ta)—a corrosion-resistant material—may be employed. Indeed, tantalum may be useful for implant fabrication according to the present disclosure because it is generally immune to the action of body liquids and is non-irritating. Titanium is a second transition metal that is corrosion resistant, offers high stiffness and is physiologically inert, thereby enhancing its usefulness according to the present disclosure. Titanium and tantalum have the unusual ability to osseointegrate. Furthermore, the anatomical position of disc implants fabricated from these metals may be easily analyzed by conventional imaging methods.

Exemplary ceramic materials for use according to the present disclosure include, but are not limited to, bio-inert ceramics (alumina ($Al_2O_3$), partially stabilized zirconia ($ZrO_2$), silicon nitride ($Si_3N_4$), bioactive ceramics (hydroxyapatite ($Ca_{10}(PO_4)_6(OH)_2$) and bioglasses), and resorbable ceramics (e.g., calcium phosphate ceramics such as tricalcium phosphate, $Ca_3(PO_4)_2$). Apatite refers to a group of phosphate minerals, usually referred to as hydroxylapatite, fluorapatite, and chlorapatite, named for high concentrations of OH—, F—, or Cl— ions, respectively, in the crystal lattice. Hydroxylapatite is the major component of tooth enamel and a large component of bone material. Hydroxylapatite is a naturally occurring form of calcium apatite with the formula $Ca_5(PO_4)_3(OH)$, but is usually written $Ca_{10}(PO_4)_6(OH)_2$ to denote that the crystal unit cell comprises two molecules. Hydroxylapaptite is easily accepted by the recipient and provides substantial stimulation of bone in-growth.

Most of the calcium phosphate ceramics are crystalline substances. The crystals are subjected to heat treatment at high temperatures, and sintered to produce a bioceramic material. Chemically, they are hydroxyapatite, tricalcium phosphate, or mixtures of the two. They are generally supplied as powders, granules, or porous or non-porous blocks.

Tricalcium phosphate is more porous than hydroxyapatite, and is biodegraded ten to twenty times faster. The sintering temperature also has an influence on the behavior of the finished product. Depending on manufacturing conditions, tricalcium phosphate will be totally resorbed within a few months, or take several years to be removed by bioresorption. In the body, it is partially converted to hydroxyapatite, which is biodegraded more slowly. In exemplary embodiments of the present disclosure, artificial bone material is employed, such as resorbable ceramic granules and resorbable tricalcium phosphate (TCP) ceramic granules.

The disclosed spinal implant may further be fabricated, in whole or in part, using glassy and pyrolytic carbon, which is highly efficient for stimulating bone fusion.

Exemplary polymers for use, in whole or in part, in fabricating spinal implants according to the present disclosure may be selected from, but are not limited to, the group of polylactides (PLA), polyglycolides (PGA), polyanhydrides, polyorthoesters, poly(D,L-lactic acid), poly(lactide-co-glycolide) (PLGA), poly-D,L-lactic acid-poly(ethylene glycol), polyphosphates, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(methacrylic acid), ultra high molecular weight polyethylene (UHMWPE), polyether ether ketones (PEEK) and polyether ketone ketones (PEKK). Preferred polymers according to the present disclosure include PEEK and PEKK. According to exemplary embodiments, a polymeric element (e.g., sheet, block and/or surface treatment) may be positioned between opposing metallic surfaces according to the present disclosure.

Exemplary bone for use, in whole or in part, in fabricating spinal implants according to the present disclosure may be selected from the group of xenograft, allograft and autograft. Preferred bone according to the present disclosure include xenograft and allograft.

The disclosed implant may be fabricated from one or more suitable materials. Thus, in exemplary embodiments, the disclosed spinal implant is made of at least one of the materials mentioned above. In further embodiments, the disclosed implant is made of at least two different materials. Either material may constitute such as between 1 and 90 percent of the total volume of the entire implant. Thus, one material may constitute 1-10%, 10-20%, 20-30%, 30-40%, 40-50%, 50-60%, 60-70%, 70-80% or 80-90% of the total volume of the entire implant. The elements of the implant may comprise a central core of a metal surrounded by a layer of resorbable ceramic material. In further embodiments, the disclosed implant is made of at least three different materials.

The resilience of the material of the disc implant is preferably of an order similar to the resilience of bone. In addition, one or more elements or part of elements may be covered by a coating layer of a particular material in order to optimize function.

e. Coating

Coating of the implant can be performed to protect the implant from body fluids, including blood at the time of implantation as well as in a period followed implantation. A coating may alternatively or in addition be used for controlling bone growth in the vicinity of the implant by including suitable compounds.

In exemplary embodiments, the disclosed implant may be coated on the outer fusion surface, the internal coupling surfaces or the internal surface of the openings of the elements or any part of each surface or any combination of surfaces. In a preferred embodiment, the internal surface of the openings is coated.

The coating generally includes at least one layer of a coating material. The coating material may be selected from any suitable material. Thus, the coating may include osteoinductive and/or osteogenic agent(s) as described here below. The coating may also take the form of a suitable polymeric material, e.g., a material that minimizes metal-to-metal contact of the first and second inter-vertebral elements. The coating may further include one or more antibiotics.

By "coated" is meant that the coating material may be situated only on the outside of the coated surface. The thickness of the coating is generally selected based on the desired function and properties of the coating, and may have a thickness of less than 1 mm, less than 0.5 mm, or less than 0.25 mm. The thickness of the coating may also vary along the surface of the disclosed implant, e.g., at different surface points of the implant. The coating of the disclosed disc implants may be performed by any suitable coating method, e.g., by dipping the elements into a solution of the coating material for a predetermined time. The coating material may also be sprayed onto the implant; another possibility is to apply the said coating by brushing.

f. Coating Material

In exemplary embodiments of the present disclosure, one or more protective coatings may be provided on the disclosed spinal implants, the materials for such protective coating(s) being selected from, but not limited to, the group of polylactides (PLA's), polyglycolides (PGA's), polyanhydrides, polyorthoesters, poly(D,L-lactic acid), poly(lacide-co-glycolide) (PLGA), poly-D,L-lactic acid-polyethylene glycol, polyphosphates, poly(lactide-co-glycolide) composited with gelatine sponge, poly(2-hydroxy ethyl methacrylate), poly (N-vinyl pyrrolidone), ethylene vinyl acetate (EVA), poly (methyl methacrylate), poly(vinyl alcohol), poly(acrylic acid), polyacrylamide, poly(ethylene-co-vinyl acetate), poly (ethylene glycol), poly(methacrylic acid), Homopolymers of L-PLA and poly-caprolactone (PCL), poly(orthoesters), like poly(anhydrides) and pseudo-poly(amino acids). The disclosed polymeric materials may advantageously limit and/or eliminate metal-to-metal contact between first and second inter-vertebral elements according to the present disclosure.

In further exemplary embodiments, the coating(s) may contain biologically active components, e.g. osteoinductive and/or osteogenic agent(s) (such as hydroxyapatite and/or tricalcium phosphate) or antibiotics. As examples, the inclusion of osteoinductive and/or osteogenic agents in the coating may induce early osteogenic processes, e.g., chemotaxis of specific cell classes, while the inclusion of antibiotics may reduce or prevent microbial infection.

Osteoinductive and/or osteogenic agents—which also can be denoted as and/or include "growth factors"—are generally proteins that bind to receptors on the cell surface, with the primary result of activating cell migration, cellular proliferation and/or differentiation. Many osteoinductive and/or osteogenic agents are quite versatile, stimulating cellular division in numerous different cell types, while others are specific to a particular cell-type.

Materials that are considered osteoinductive generally contain morphogens, such as bone morphogenetic proteins. Morphogens initiate tissue and organ system development by stimulating undifferentiated cells to convert phenotypically. Suitable growth factors which may be used according to the present disclosure include, but are not limited to, tissue growth enhancing substances, such as growth and differentiation factors, that include platelet-derived growth factor (PDGF), transforming growth factor (TGF), acidic and basic fibroblast growth factor (FGF), insulin-like growth factor (IGF), bone morphogenetic proteins (BMPs) and combinations thereof.

In exemplary embodiments of the present disclosure, the osteoinductive and/or osteogenic agent may be selected from the group of bone growth factors: platelet-derived growth factor (PDGF) (PDGF-AA, -AB, -BB), insulin-like growth factors I and II (IGF-I, IGF-II), fibroblast growth factors (FGFs) (acidic FGF-aFGF, basic FGF-bFGF), transforming growth factor beta (TGF-B) (TGF-B (TGF-Bs 1, 2, 3, 4, and 5)), osteoinduction and bone morphogenetic protein (BMP) (BMP-1, BMP-2, BMP-3, BMP-4, BMP-5, BMP-6, BMP-7, BMP-8, BMP-9, BMP-10, BMP-11, BMP-12), epidermal growth factor (EGF), cementum-derived growth factor (CGF), parathyroid hormone-related protein (PTHrP). Preferred growth factors or osteoinductive and/or osteogenic agents include the bone morphogenetic proteins (BMP-1, BMP-2, BMP-3, BMP-4, BMP-5, BMP-6, BMP-7, BMP-8, BMP-9, BMP-10, BMP-11, BMP-12) and platelet-derived growth factors (PDGF) (PDGF-AA, -AB, -BB).

Coatings for use according to the present disclosure may include at least one osteoinductive and/or osteogenic agent, and optionally more than one such agent, e.g., 2 agents, 3 agents, 4 agents, 5 agents, 6 agents, 7 agents, 8 agents, 9 agents, 10 agents or more. Exemplary implementations of the present disclosure include 1, 2 or 3 osteoinductive and/or osteogenic agents. More preferred implementations include 1 or 2 osteoinductive and/or osteogenic agents.

One or more layers of the coating material may be placed on or applied to the disclosed implant. In implementations where two or more layers are placed/applied, these layers may be equal or different in composition and one or more layers may contain osteoinductive and/or osteogenic agent(s) or other biologically active components.

Alternatively, the osteoinductive and/or osteogenic agents may be comprised of one or more of the materials forming the elements of the disclosed disc implant. Thus, the implant may be designed for secretion of one or more of the osteoinductive and/or osteogenic agents, whereby stimulation of bone growth is directed by or otherwise initiated/supported by the elements of the disc implant. The disclosed disc implant preferably encourages bone formation.

g. Osseointegrative Section(s)/Opening(s)

The first and second inter-vertebral elements of the disclosed disc implants generally include and/or define osseointegrative sections. Such sections generally have a capacity for stimulating and directing bone growth. For example, the inter-vertebral elements may be adapted to stimulate bone growth for fusion of the outer surface of each such inter-vertebral element relative to the neighboring vertebral element(s). The disclosed inter-vertebral elements are also generally adapted to further direct bone in-growth for fixation over time of the inter-vertebral elements relative to each other. Thus, the temporal movability of the first and second inter-vertebral elements of the disc implant is displaced by fixation of the first and second inter-vertebral elements within a period of time after insertion/implantation. Thus, the inclusion of osseointegrative sections also enables and/or facilitates fixation of the first and second inter-vertebral elements relative to each other over time.

The inner and outer surface of the first and second inter-vertebral elements may include and/or define osseointegrative sections designed for optimization of bone in-growth according to the present disclosure. As described here below, the osseointegrative sections may be defined, in whole or in part, by openings, such as holes and/or incisions in the surface of the inter-vertebral elements which provide entry points for bone in-growth. The osseointegrative sections may also include suitable osteoinductive and/or osteogenic agents, and/or osteoinductive and/or osteogenic materials. Implementations of the present disclosure where openings formed in the intervertebral elements include osteoinductive and/or osteogenic agents, and/or osteoinductive and/or osteogenic materials within such openings are referred to as "filled" openings.

In exemplary embodiments of the present disclosure, the disclosed inter-vertebral elements include or define one or more openings suitable for bone in-growth, such openings being sufficiently large to (i) allow entrance of osteoblasts and osteogenic cells and (ii) sustain the viability of such osteoblasts and osteogenic cells. The openings generally proceed or extend through the disclosed inter-vertebral elements and allow in-growth of bone through the elements. The openings may have any shape or size compatible with the design/geometry of the inter-vertebral elements of the disc implant. For example, the openings may constitute or define straight (or substantially straight) channels that extend through the inter-vertebral element(s). In exemplary embodiments, the diameter(s) of the opening(s) may vary as the channel extends through the inter-vertebral element, e.g., the diameter of the opening channels may be expanded with an internal void in the element.

The surface area of the intervertebral elements occupied by the openings is generally sufficient to support desired levels of bone in-growth to achieve fixation of the first and second intervertebral elements relative to each other over time. However, it is noted that such bone in-growth is generally not limited to bone growth through such openings, but is complemented by bone in-growth that extends along or around the outer edges of the inter-vertebral elements. In exemplary embodiments of the present disclosure, the openings occupy at least 5% of the surface area of the first and/or second intervertebral element(s), and in further exemplary embodiments, at least 10% or at least 15% of such surface are in order to permit/stimulate sufficient in-growth of bone. In further exemplary embodiments, the surface area of the first and/or second inter-vertebral element(s) that is occupied by the openings/holes is 10-40% of such surface area, e.g., 20-35% thereof. The openings and the internal void volume may constitute 10-90% of the bulk volume of the inter-vertebral elements of the disclosed disc implants, e.g., 20-80%, 30-70%, 40-60% and/or 30-60% of the bulk volume of the inter-vertebral elements.

When referring to the bulk volume of the inter-vertebral elements, the volume of the coupling zone is not included, but merely the approximate volume of the individual inter-vertebral elements, including the volume of the openings and internal void volume, if present.

In exemplary embodiments of the present disclosure, the one or more openings of the first and second inter-vertebral elements are opposing each other, i.e., substantially aligned, when the inter-vertebral elements are engaged with each other via the coupling means/mechanism. An opposed/aligned arrangement of such openings provides optimal conditions for promoting bone in-growth though both inter-vertebral elements to achieve desired objects of the present disclosure, e.g., fusion of the disc implant at each outer surface relative to adjacent vertebral bodies and fixation of the first and second inter-vertebral elements of the disc implant elements relative to each other when bone tissue is formed in the coupling zone formed/defined by the internal surfaces of the inter-vertebral elements.

Minor openings on the surface of one or both inter-vertebral elements may be denoted as "pores", which affect the capabilities of the implant to stimulate bone growth at the surfaces. The level of porosity, pore size distribution, pore morphology, and the degree of pore interconnectivity of implants significantly influences the extent of bone growth. An exemplary pore volume on the outer surface of the first and/or second inter-vertebral body to encourage osteoinduction is 150-500 mm$^3$. In addition, the outer surfaces of one or both inter-vertebral elements may further be rough, rugged or granular to further promote fusion relative to adjacent vertebral bodies.

h. Incisions/Circumferential Inset Regions

Alternative to or in combination with openings as described above, the disclosed inter-vertebral element(s) may include or define incisions or circumferential inset regions of various shapes/geometries to facilitate bone in-growth and fixation of the first and second inter-vertebral elements over time. Thus, in exemplary embodiments of the present disclosure, openings in and through the intervertebral elements may be combined with incisions/circumferential inset regions to promote/facilitate desired levels of bone in-growth. For example, the disclosed openings and incisions/circumferential inset regions may stimulate osteoconduction by providing a scaffold for the cells to move into and create new bone.

As noted above, the inter-vertebral elements of the disclosed disc implant may be fabricated from one or more different materials. In exemplary embodiments of the present disclosure, a filling may be located in the openings and/or incisions/circumferential inset regions of the intervertebral elements of the disc implant, whereby a filled implant is obtained. The filling may include material(s) suitable for directing and/or stimulating osteogenic activity and or inhibition of bone resorption. For example, auto and/or allograft of bone or demineralized bone matrix (DBM) may be used as a filling material. Artificial bone materials, such as ceramic materials, may also be employed. Resorbable materials, such as resorbable ceramic granules, may also be utilized, allowing and/or facilitating bone formation in the openings and/or incisions/circumferential inset regions within a suitable time. Thus, the disclosed spinal implant may be filled with resorbable materials, such as resorbable ceramic granules, which by suitable packaging may aid in the timing and/or extent of bone in-growth. In further exemplary embodiments, the filling may include osteoinductive and/or osteogenic agent(s), as described in relation to coatings.

i. Temporal Movability

The spinal disc implant according to the present disclosure advantageously fuses with the surrounding vertebrae. In particular, the outer fusion surface of the first and second inter-vertebral elements are suited for fusion with neighboring bones/vertebral bodies.

Aside from the noted fusion relative to adjacent bones/vertebral bodies, the characteristics and arrangement of the disclosed first and second inter-vertebral elements advantageously provide a temporal movability of the elements relative to each other post-implantation. However, the elements of the disclosed disc implant are constructed to stimulate osteoconduction, i.e., the channeling of bone growth through the inter-vertebral elements of the implant. This bone in-growth leads to fixation of the first and second inter-vertebral elements relative to each other over time and thereby displaces/overrides the temporal movability of the first and second inter-vertebral elements of the disc implant.

The temporal movability of the first and second inter-vertebral elements is beneficially displaced/overridden by fixation of the disc implant in a physiologically acceptable position. This physiologically acceptable position of the disclosed implant is achieved during the days to weeks following insertion/implantation, rather than at the point of implantation. More particularly, the relative positions of the first and second inter-vertebral elements of the implant will adapt—based on the movable coupling therebetween—to a position affected by and/or responsive to the load, posture and spinal movements of the recipient. Thus, fixation of the first and second inter-vertebral elements relative to each other will occur over a period of time post-implantation by bone in-growth through and/or around the implant. The natural and patient-specific fixation of the disclosed implant, rather than establishing a fixed position determined during the surgical procedure in connection with insertion/implantation of the implant, is highly advantageous.

In an exemplary embodiment of the present disclosure, fixation of the first and second inter-vertebral elements relative to each other—leading to the formation of a fixed implant—is caused by bone in-growth which occurs predominantly through the osseointegrative section(s) of the inter-vertebral elements of the disc implant.

In exemplary embodiments of the present disclosure, the first and second inter-vertebral elements of the disc implant remain relatively movable for periods of time post-implantation, e.g., more than 8 hours, more than 16 hours, and/or more than 24 hours. In further exemplary embodiments, the first and second inter-vertebral elements of the disc implant remain relatively movable for periods of time post-implantation that extend for at least 1 day, at least 2 days, at least 3 days, and/or more than 4 or 5 days. In embodiments of the present disclosure, first and second inter-vertebral elements of the disc implant elements retain movability for 1 to 90 days, 3-30 days and/or 20-25 days after insertion, i.e., post-implantation.

In further exemplary embodiments of the present disclosure, the disclosed disc implant is converted to a fixed implant, wherein the relative movability of the first and second inter-vertebral elements of the disc implant are fixed relative to each other, in less than 18 months, or less than 12 months, or less than 8 months, or less than 6 months after insertion/implantation. In exemplary implementations, the disclosed inter-vertebral elements are fixed relative to each other within 3-12 months, within 5-10 months and/or within 6-9 months after insertion/implantation.

As the fixation of the disclosed disc implant is a gradual process based on ongoing bone in-growth, the degree of fixation or movability may be evaluated after implantation. It is further contemplated that the process of fixation will occur with different kinetics in different subjects. In exemplary implementations, the disclosed disc implant can be expected to be at least 65% fixed in the first several weeks post-implantation, or at least 70% fixed in the first several weeks post-implantation, or at least 75% fixed in the first several weeks post-implantation, or at least 80% fixed in the first several weeks post-implantation, or at least 85% fixed in the first several weeks post-implantation. In exemplary embodiments, the disclosed disc implant is at least 90% fixed one (1) month post-implantation, or at least 92% fixed one (1) month post-implantation, or at least 95% fixed one (1) month post-implantation. Ultimately, the disclosed disc implant achieves 100% fixation.

j. Methods of Treatment

An individual suffering from lower back pain and/or leg pain resulting from spine injury or other disease may obtain relief by an insertion of a disc implant. An aspect of the present disclosure relates to method(s) of treatment of an individual in need thereof, wherein the method includes insertion of a disc implant, such disc implant including first and second inter-vertebral elements that remain relatively movable for a period of time post-implantation, e.g., at least 1 day after insertion/implantation, and the implant is converted into a fixed implant after a period of time, e.g., less than 18 month after insertion. The disclosed method(s) may be achieved through anterior, lateral, posterior and or transforaminal insertion. In addition, the disclosed method(s) may be combined with insertion/implantation (or pre-existing) posterior stabilization means/devices. The posterior stabilization can be in form of flexible (dynamic), semi-rigid or rigid implants, such as pedicle screws, interspinous process spacers or facet joint screws or any other fixation/stabilization method known or subsequently developed in the art.

The first and second inter-vertebral elements may be introduced simultaneously, i.e., in a "pre-assembled" configuration. Alternatively, the first and second inter-vertebral elements may be introduced sequentially, with side-by-side assembly/positioning of the first and second inter-vertebral elements being undertaken and/or achieved in situ. To the extent a third element, e.g., a polymeric sheet or block, is positioned between the first and second inter-vertebral elements, such intermediate third element may be positioned relative to the first and/or second inter-vertebral element prior to anatomical positioning of the implant in the desired spinal location, or may be introduced sequentially, e.g., after the first and/or second inter-vertebral element is introduced to the anatomical location.

2. Exemplary Disc Implant(s)

In exemplary embodiments of the present disclosure, the disclosed spinal disc implant includes a first inter-vertebral element having a first outer fusion surface and an internal coupling surface, a second inter-vertebral element having a second outer fusion surface and an internal coupling surface, and a coupling means/mechanism for connecting the first and second inter vertebral elements. Each inter-vertebral element generally includes one or more osseointegrative sections that facilitate fixation of the first and second elements relative to each other over time. In addition, exemplary implementations of the disclosed spinal disc include one or more fusion blocks that are adapted to be joined relative to the first and/or second inter-vertebral elements. The first and second inter-vertebral elements of the disclosed disc implant generally remain relatively movable for at least one (1) day after insertion/implantation, i.e., movable relative to the coupling means/mechanism, and the implant is converted into a fixed implant after a period of time post-implantations, e.g., less than 18 month after insertion/implantation. An intermediate polymeric element (or intermediate polymeric elements) may be provided to reduce and/or eliminate potential metal-to-metal contact associated with the first and second inter-vertebral elements.

With reference to FIGS. 1-11, an initial exemplary disc implant 10 (and associated components thereof) is schematically depicted. Thus, with initial reference to FIG. 1, an isometric view of disc implant 10 is provided, such implant functioning as a "fusion implant" after a period of time post-implantation. Disc implant 10 includes a first inter-vertebral element 12 and a second inter-vertebral element 14 that are coupled with respect to each other, i.e., assembled such that the inner surfaces thereof are juxtaposed in a facing alignment. Disc implant 10 further includes a first fusion block 16 and a second fusion block 18 which are mounted relative to the first and second inter-vertebral elements 12, 14. More particularly, first and second fusion blocks 16, 18 are positioned in respective corner regions of disc implant 10.

The outer face 20 of second inter-vertebral element 14 is visible in FIG. 1 and includes structural features and/or functional attributes that facilitate fixation of disc implant 10 relative to adjacent anatomical structure(s), e.g., an adjacent vertebral body. It is expressly contemplated that the outer surface of first inter-vertebral element 12—which is not visible in FIG. 1—may include the same or different surface features, attributes and/or treatments as are described below with reference to outer surface 20 of second inter-vertebral element 14 according to the present disclosure.

Thus, for example, outer face 20 (and/or the outer face of first inter-vertebral element 12) may include and/or define a plurality of generally pyramidal formations 22 that are substantially cover outer face 20 of second inter-vertebral element. Depending on material, pyramidal formations 22 may have either a sharp point or a rounded point for contacting adjacent bone. It is further contemplated that a combination of sharp/rounded points may be employed to facilitate interaction and/or fixation with respect to adjacent bone. Additional and/or alternative surfaces geometries may be employed on outer surface 20, e.g., a plasma sprayed outer surface 20, a uniformly or irregularly roughened outer surface 20, a curved outer surface 20 or a flat outer surface 20 may be employed in whole or in part. In any of these cases, the bone fixation behavior of outer surface 20 may be enhanced by deposition of a variety of bone-friendly materials, such as hydroxylapatite, tricalcium phosphate, and mixtures thereof on outer surface 20. In addition, fixation performance of outer surface 20 may be enhanced through selection of appropriate materials of construction, e.g., titanium, titanium alloy and/or tantalum. Still further, chemicals and/or coatings may be applied to outer surface 20 to enhance formation of bone adjacent to second inter-vertebral element 14. As noted above, each of the surface features, attributes and/or treatments described herein with reference to outer surface 20 of second inter-vertebral element 14 apply with equal force to the outer surface of first inter-vertebral element 12 (which is not visible in FIG. 1).

In addition to surface geometries to enhance fixation, a number of features could be added to the outer surface(s) of the first and/or second inter-vertebral elements 12, 14 to enhance fixation. For example, a keel, such as disclosed in U.S. Pat. No. 5,314,477, or screws, such as disclosed in U.S. Pat. No. 5,556,431 (wherein one or more screws is passed through a component into the bone and thereby holds the component fixed to the bone) may be employed with respect to the outer surface(s) of first and/or second inter-vertebral elements 12, 14 without departing from the spirit or scope of the present disclosure. The relevant contents of the noted '477 patent and the '431 patent are incorporated herein by reference.

In terms of the assembly of disc implant 10 of FIG. 1, it is noted that the first and second inter-vertebral elements 12, 14 are generally coupled relative to each other and anatomically simultaneously inserted/implanted in a desired anatomical location. However, in alternative implementations, the first and second inter-vertebral elements 12, 14 may be introduced to a desired anatomical location sequentially and assembled in situ. Thereafter, fusion blocks 16, 18 may be introduced to the anatomical region and mounted relative to the first and second inter-vertebral elements 12, 14, as described in greater detail below.

With reference to FIGS. 1-8, it is noted that each of first and second intervertebral elements 12, 14 define a plurality of openings that extend through their respective bodies, such openings functioning as osseointegrative sections of first and second intervertebral elements 12, 14. Thus, first intervertebral element 12 defines openings 24, 26, whereas second intervertebral element 14 defines openings 28, 30. The exemplary openings 24, 26, 28, 30 of disc implant 10 depicted in FIGS. 1-5 are substantially irregular in geometry—defining what might be termed "ear" shapes—but the present disclosure is not limited by or to the exemplary opening geometries depicted in FIGS. 1-5. Of note, the openings associated with first intervertebral element 12 (openings 24, 26) are generally configured and dimensioned to substantially align with the openings associated with second intervertebral element 14 (openings 28, 30) when the first and second intervertebral elements 12, 14 are assembled, as shown in FIG. 1.

In the exemplary embodiment of FIG. 1, the openings associated with each of first and second inter-vertebral elements 12, 14 encompass a substantial portion of the surface areas of the opposed faces thereof, e.g., greater than 50% of such surface areas. In this way, bone in-growth into disc implant 10 so as to "fix" first and second intervertebral elements 12, 14 relative to each other is encouraged. However, it is to be understood that the present disclosure is not limited by or to implementations wherein the openings constitute openings at the noted level. For example, the openings may constitute a lesser percentage of the surface area, e.g., on the order of 10%, or an intermediate level, e.g., between 10% and 50%. Still further, the openings may constitute a greater percentage of the surface area, e.g., greater than 50%. It is further noted that bone in-growth may be achieved in exemplary embodiments without the provision of openings in the surface area, e.g., wherein fusion occurs through bone growth at least in part anterior to the first and second inter-vertebral elements.

Figure 2:
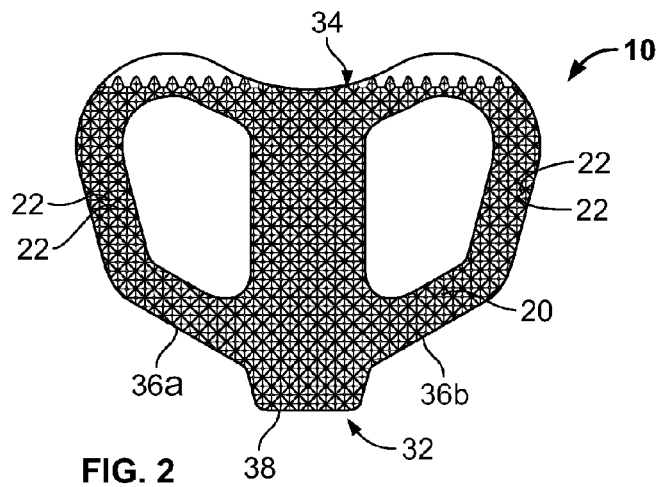
FIG. 2 is a top view of a first component/intervertebral element of the exemplary implant of FIG. 1.

With particular reference to FIG. 2, a top view of disc implant 10 is provided which primarily depicts the outer face 20 of second inter-vertebral element 12. As is readily apparent from the various views of FIGS. 1-5, the outer profiles of the first and second inter-vertebral elements 12, 14 are the same (or substantially the same) such that, when coupled/assembled, a substantially uniform outer edge/profile is defined. Thus, the combined/assembled profiles of the first and second inter-vertebral elements of disc implant 10 define an anterior edge 32 and a posterior edge 34. Anterior edge 32 may be broken into three (3) sub-regions for description purposes: anterolateral edge 36a and anterolateral edge 36b that surround central anterior edge 38. The recessed geometry associated with anterolateral edges 36a, 36b relative to central edge 38 allows placement of bone materials and/or other desired materials anterior to disc implant 10 in a location that may facilitate and/or induce bone fusion. It is this recessed region adjacent anterolateral edges 36a, 36b that advantageously accommodates placement/coupling of fusion blocks 16, 18 as described in further detail below.

Figure 3:
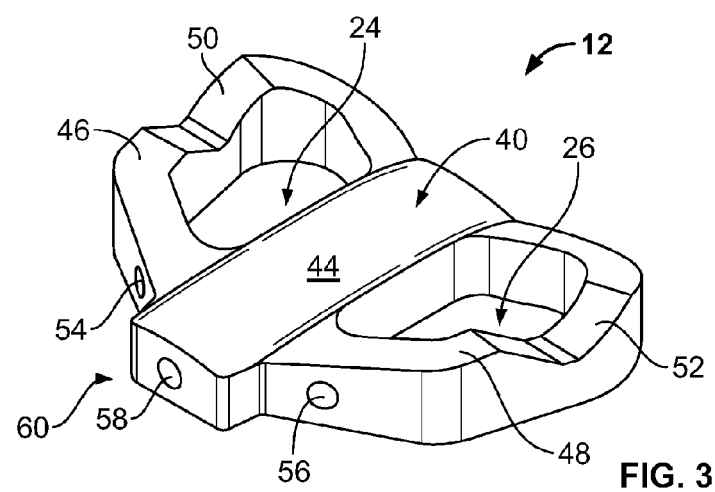
FIG. 3 is an oblique view of a second component/intervertebral element of the exemplary implant of FIG. 1.

With reference to the coupling mechanism of exemplary disc implant 10, it is noted that the first and second inter-vertebral elements 12, 14 define cooperative inner faces 40, 42 that facilitate relative movement between first and second inter-vertebral elements 12, 14 for an initial period of time post-implantation of spinal disc 10. Thus, in the exemplary embodiment of FIGS. 1-5 and as best seen in FIG. 3, inner face 40 of first intervertebral element 12 defines a central region 44 and two wing regions 46, 48. The central region 44 and wing region 46 together form or bound opening 24, whereas central region 44 and wing region 48 form or bound opening 26. A pair of slots 50, 52 are formed in outer wing regions 46, 48, respectively. In addition, insertion holes 54, 56, 58 are formed in the anterior face 60 of first inter-vertebral element 12. Insertion holes 54, 56, 58 may be used to facilitate interaction with a placement tool (not pictured) for clinical delivery of disc implant 10 to a desired anatomical location. In addition, insertion holes 54, 56 are positioned to accommodate mounting of fusion blocks 16, 18, respectively. Alternative fusion block geometries and/or designs are contemplated according to the present disclosure. For example, the fusion block(s) may include surface features and/or geometries that facilitate bone in-growth. Thus, as will be readily apparent to persons skilled in the art, the present disclosure encompasses fusion block(s) of substantially any design/geometry provided such fusion block(s) are dimensioned and configured for placement in the available anterior space.

Figure 4:
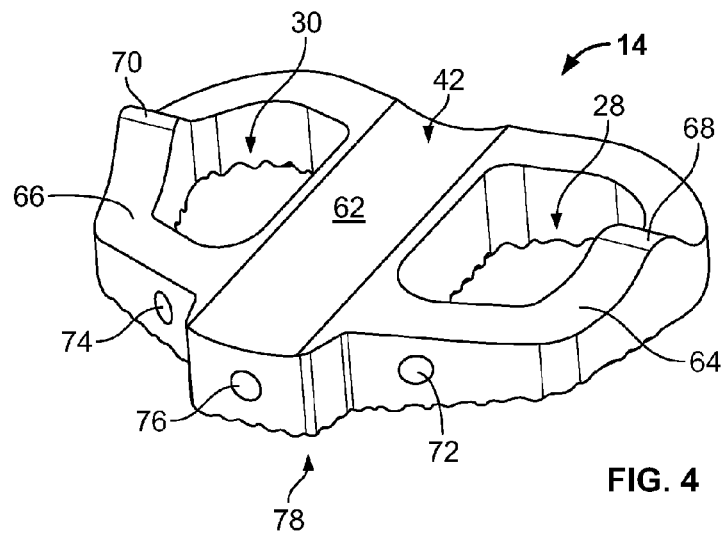
FIG. 4 is an oblique view of the first component/intervertebral element of the exemplary implant of FIGS. 1 and 2, showing the geometry of such component/element that faces the second component/intervertebral element when assembled with respect thereto.

FIG. 4 provides an oblique view of the inner face 42 of second inter-vertebral element 14. The inner face 42 of second intervertebral element 14 defines a central region 62 and two wing regions 64, 66. The central region 62 and wing region 64 together form or bound opening 28, whereas central region 62 and wing region 66 form or bound opening 30. A pair of upstanding bosses 68, 70 are formed in outer wing regions 64, 66, respectively. In addition, insertion holes 72, 74, 76 are formed in the anterior face 78 of second inter-vertebral element 14. Insertion holes 72, 74, 76 may be used to facilitate interaction with a placement tool (not pictured) for clinical delivery of disc implant 10 to a desired anatomical location. In addition, insertion holes 72, 74 are positioned to accommodate mounting of fusion blocks 18, 16, respectively.

The first and second inter-vertebral elements of disc implant 10 are advantageously movably coupled with respect to each other when the inner face 40 of first inter-vertebral element 12 is brought into abutting engagement with the inner face 42 of second inter-vertebral element. When brought into the noted abutting engagement, opening 24 of first inter-vertebral element 12 substantially aligns with opening 28 of second inter-vertebral element 14, and opening 26 of first inter-vertebral element 12 substantially aligns with opening 30 of second inter-vertebral element 14. In addition, upstanding boss 68 of second inter-vertebral element 14 aligns/cooperates with slot 50 of first inter-vertebral element 12, and upstanding boss 70 of second inter-vertebral element 14 aligns/cooperates with slot 52 of first inter-vertebral element 12. The alignment/cooperation of upstanding boss 70 and slot 52 is schematically depicted in the side view of FIG. 8. Still further, central region 44 of first inter-vertebral element 12 is in abutting relationship with central region 62 of second inter-vertebral element 14 to define an articulating region 90 therebetween (see FIG. 6).

Generally, the articulating region 90 provides primary contact between the first and second inter-vertebral elements 12, 14. The openings 24, 26 formed in wing regions 46, 48 of the first inter-vertebral element 12 and the openings 28, 30 formed in wing regions 64, 66 of the second inter-vertebral element 14 may receive bone materials (or other materials) to facilitate bone in-growth therethrough. In addition, interaction/contact between the respective wing regions of the first and second inter-vertebral elements 12, 14 advantageously function to limit lateral bending therebetween. Further, interaction between the bosses 68, 70 of the second inter-vertebral element 14 and the slots 50, 52 of the first inter-vertebral element 12 serve, inter alia, to resist or limit anterior-posterior translation of either the first or second intervertebral element 12, 14 with respect to the other, as well as resist or limit axial rotation of either the first or second intervertebral element 12, 14 with respect to the other. In exemplary embodiments of the present disclosure, disc implant 10 is symmetric (or substantially symmetric) about an anterior-posterior plane passing through the central insertion holes 58, 76, i.e., along the plane defined by articulating region 90.

Figure 5:
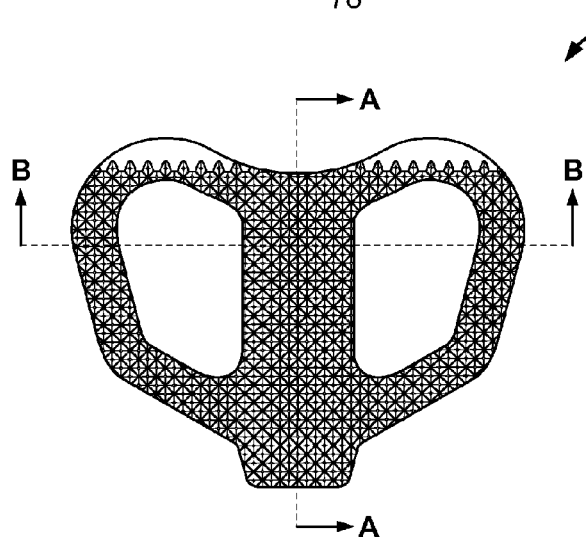
FIG. 5 is a top view of the first and second components/elements of the exemplary implant of FIGS. 1-4 in an assembled position.
Figure 6:
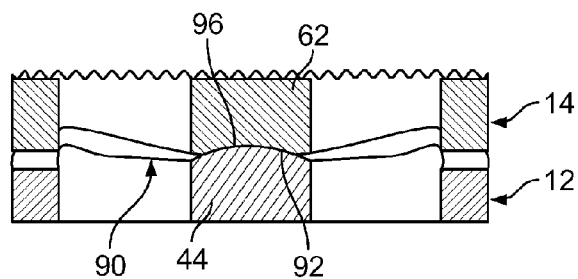
FIG. 6 is a front sectional view of the first and second components/elements in the assembled position taken along line B-B in FIG. 5.
Figure 7:
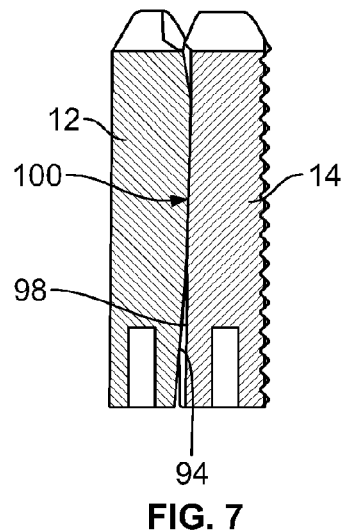
FIG. 7 is a side sectional view of the first and second components/elements in the assembled position taken along line A-A in FIG. 5.

FIGS. 6 and 7 show cross sections through an aligned assembly of the first and second inter-vertebral elements 12, 14 of exemplary disc implant 10. With particular reference to FIG. 5, the planes along which the sectional views of FIGS. 6 and 7 are identified. Thus, the sectional view of FIG. 6 is taken along the plane defined by line B-B in FIG. 5, and the sectional view of FIG. 7 is taken along the line A-A in FIG. 5. The central region 44 of the first inter-vertebral element 12 is generally defined as a swept surface with a first profile 92 in the medial lateral direction (see FIG. 6), and a second profile 94 in the anterior-posterior direction (see FIG. 7). It is generally preferable that the first profile 92 in the medial-lateral direction be a single arc. It is also generally preferable that the profile 94 in the anterior-posterior direction be composed of at least two arcs. This arc combination advantageously allows for normal anatomical motion of a patient in flexion-extension, while controlling contact forces between the first and second inter-vertebral elements 12, 14. However, the present disclosure is not limited by or to the arc-based implementations described with reference to the exemplary first inter-vertebral element 12 of FIGS. 1-8.

The central region 62 of the second inter-vertebral element is also generally defined as a swept surface with a first profile 96 in the medial lateral direction (see FIG. 6), and a second profile 98 in the anterior posterior direction (see FIG. 7). It is generally preferable that the first profile 96 be a single arc. It is also generally preferable that the second profile 98 be composed of a line. However, as with the first inter-vertebral element 12, the present disclosure is not limited by or to the arc-based implementations described with reference to the exemplary second inter-vertebral element 14 of FIGS. 1-8.

So as to reduce contact stresses, it is generally preferable that the radii of the mating arcs 92, 96 in the medial lateral direction be of similar (but not the same) value, thereby reducing the contact stress between the first and second inter-vertebral elements 12, 14. Also, the extent of the profile of the first inter-vertebral element 12 is generally greater than the second inter-vertebral element 14 to enable/facilitate rotation of the second inter-vertebral element 14 relative to the first inter-vertebral element 12 prior to contact between a wing 46, 48 of the first inter-vertebral element 12 and an abutting wing 64, 66 of the second inter-vertebral element 14.

As seen in FIG. 7, there is also an advantageous relationship between the profiles in the anterior-posterior direction of exemplary first and second inter-vertebral elements 12, 14 of the present disclosure. In contrast to the medial-lateral profiles, the anterior-posterior curves are generally not as closely matched. For example, profile 94 of the first inter-vertebral element 12 is typically matched with the anterior-posterior profile 98 of the second inter-vertebral element 14. This matching of anterior-posterior profiles enables the necessary and/or desired flexion-extension motion of a patient and facilitates positional adaptability of the disclosed disc implant in an initial period post-implantation. Of note, the central regions 44, 62 of first and second inter-vertebral elements 12, 14 define a contact region 100 in the aligned position (see FIG. 7).

While exemplary profiles have been described with reference to disc implant 10, a variety of alternate profiles are contemplated. For example, medial lateral profiles 92, 96 may be formed/defined by geometries that include radiused opposing faces, elliptical opposing faces, spline-shaped opposing faces or other generally curved elements. Similarly, the anterior-posterior profiles 94, 98 may be formed/defined by geometries that include radiused opposing faces, elliptical opposing faces, spline-shaped opposing faces or other generally curved elements. It is further contemplated that the articulating geometries may be reversed/inverted, such that the disclosed geometric features and functions of the first inter-vertebral element 12 described with reference to the exemplary embodiment of FIGS. 1-8 may be associated instead with second inter-vertebral element 14, and vice versa. Thus, the geometric features/functions of profiles 92, 94 may be traded for the geometric features/functions of profiles 96, 98. However, it is noted that a reversal of the profile features described herein may not be preferable because the center of rotation of the first and second inter-vertebral elements 12, 14 would be potentially shifted away from the natural center of rotation of the spine segment, which is believed to be in the posterior half of the lower body of the spine segment.

Axial rotation motion may be enabled as between the first and second inter-vertebral elements 12, 14 during an initial period post-implantation based, at least in part, on a slight mismatch in the medial-lateral radii of opposing profiles 92, 96 of the first and second inter-vertebral elements 12, 14. However, resistance to excessive axial rotation is provided via the interaction of the slots 50, 52 of the first inter-vertebral element 12 and the cooperating bosses 68, 70 of the second inter-vertebral element 14. As shown in FIG. 3, slots 50, 52 may advantageously define a substantially V-shaped geometry. Slots 50, 52 may also define a flat bottom that is generally parallel to the outer face of the first inter-vertebral element 12. Thus, the V-shaped geometry may be formed/defined by opposed, angled walls that extend to the flat bottom.

Figure 8:
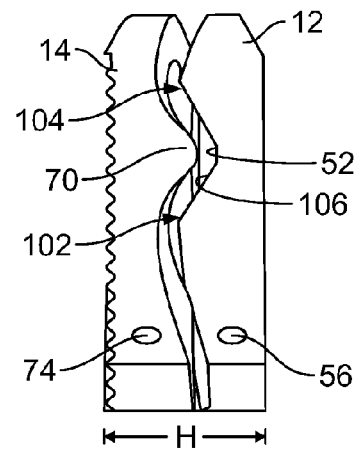
FIG. 8 is a side view of the first and second components/elements of the exemplary implant of FIGS. 1-7 in the assembled position.

The upstanding bosses 68, 70 associated with and extending from the wings 64, 66 of the second inter-vertebral element 14 generally define rounded geometric features at an upper extent thereof. In a neutral alignment of first and second inter-vertebral elements 12, 14, the upstanding bosses 68, 70 generally fit within the slots 50, 52 defined in the first inter-vertebral element 12. As shown in FIG. 8, the interaction between bosses 68, 70 and slots 50, 52 generally define an anterior gap (e.g., anterior gap 102), a posterior gap (e.g., posterior gap 104), and a distal gap (e.g., distal gap 106) between the boss and the slot. With axial rotation, the posterior gap 104 diminishes as the anterior gap 102 increases on one side of the implant 10, with the posterior gap 104 increasing and the anterior gap 102 diminishing on the second side. With continued axial rotation, an anterior gap is closed/eliminated on one side, while the posterior gap is closed on the other side of the implant. Due to the relative shape of both the slots 50, 52 and the bosses 68, 70, continued axial rotation (beyond initial contact) will force the bosses 68, 70 to ride up the side of the slots 50, 52. As the bosses 68, 70 ride up the side of the slots 50, 52, the assembled height of the first and second inter-vertebral elements 12, 14, dimensioned as "H" in FIG. 8, will increase. The increase in "H" will increase the tension in the soft tissues crossing the disc space so as to provide a resistive force countering further axial rotation.

The design of the first and second inter-vertebral elements 12, 14, and specifically the cooperating slots 50, 52 and bosses 68, 70, is generally effectuated such that the anterior and posterior gaps 102, 104 are equivalent, while the distal gap 106 may be different relative to the anterior and posterior gaps 102, 104. Of note, the anterior and posterior gaps 102, 104 generally function to limit free axial rotation of the second inter-vertebral element 14 relative to the first inter-vertebral element 12. The distal gap 106 generally functions to provide clearance which permits lateral bending of the second inter-vertebral element 14 relative to the first inter-vertebral element 12 without contact of the boss 68, 70 with the corresponding slot 50, 52.

The slots 50, 52 and bosses 68, 70, and specifically the anterior gaps 102 and the posterior gaps 104, generally determine the amount of (i) free relative anterior-posterior translation between the first and second inter-vertebral elements 12, 14, and (ii) the resistance to excessive anterior-posterior translation exhibited by disc implant 10. With reference to FIG. 8, it is noted that when the second inter-vertebral element 14 moves anteriorly relative to the first inter-vertebral element 12, the anterior gap 102 closes on both sides of the assembled disc implant 10. When the anterior gap 102 is closed completely, further anterior translation requires that the bosses 68, 70 ride up the sides of the slots 50, 52, increasing the assembled height "H", as described previously with regard to axial rotation.

Alternative geometries for the bosses 68, 70 and the slots 50, 52 are also contemplated according to the present disclosure. For example, bosses that include flat sloped faces that are generally parallel to the angled walls of the slots may be employed. Similarly, slots with curved walls and/or slots with walls that are generally perpendicular to the tops and bottoms of the first and second inter-vertebral elements 12, 14 mating to bosses with either generally rounded features or with flat sloped faces parallel to the walls of the slots may be employed.

In both flexion-extension and lateral bending, the articulating geometry of the disclosed disc implant 10 advantageously allows substantially free movement in an initial period post-implantation. This free movement in the initial implantation period allows the first and second inter-vertebral elements 12, 14 to assume a desired relative orientation, e.g., based on influences and/or forces exerted by soft tissues of the spine. Through bone in-growth, such desired relative orientation becomes fixed as such bone in-growth initially inhibits and ultimately prevents relative motion between the first and second inter-vertebral elements 12, 14, i.e., fusion is established therebetween.

3. Fusion Blocks

Figure 9:
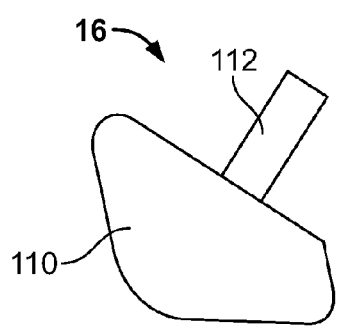
FIG. 9 is a top view of an exemplary fusion block for use in conjunction with implants according to the present disclosure.
Figure 10:
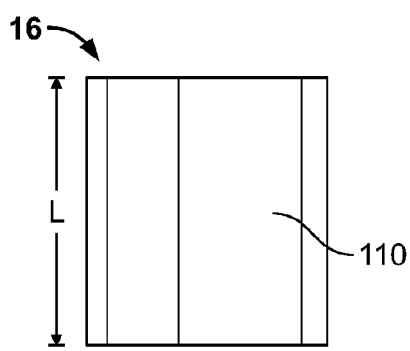
FIG. 10 is a front view of the exemplary fusion block of FIG. 9.
Figure 11:
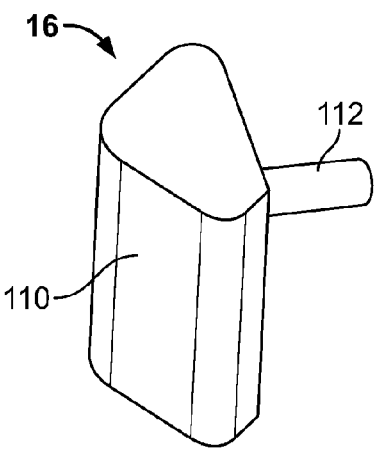
FIG. 11 is an oblique view of the exemplary fusion block of FIGS. 9 and 10.

As mentioned previously, fusion blocks 16, 18 may be used to enhance bone fusion anteriorly of disc implant. FIGS. 9, 10 and 11 provide top, front and oblique views of exemplary fusion block 16—which generally corresponds in all material respects as a mirror image to fusion block 18. Exemplary fusion block 16 generally includes two structural elements, namely a columnar body 110 and a connector stem 112. The columnar body 110 may define a non-circular column and a height "L", as shown in FIG. 10. The profile of columnar body 110 is generally complementary to the profile of the first and second inter-vertebral elements 12, 14, and fills (at least in part) the anterolateral space adjacent to anterolateral edges 36a, 36b of disc implant 10 (see FIG. 2). The height "L" of exemplary fusion block 16 is generally similar in height to the assembled height "H" of the first and second inter-vertebral elements 12, 14.

The connector stem 112 associated with fusion block 16 enables coupling/connection between fusion block 16 and either first or second inter-vertebral element 12 or 14. For example, the connector stem 112 may be received by insertion holes 54 or 56 of first inter-vertebral element 12 and/or insertion holes 72, 74 of second inter-vertebral element 14 so as to provide temporary alignment and fixation of the fusion block with respect to the first and second inter-vertebral elements 12, 14.

Figure 12:
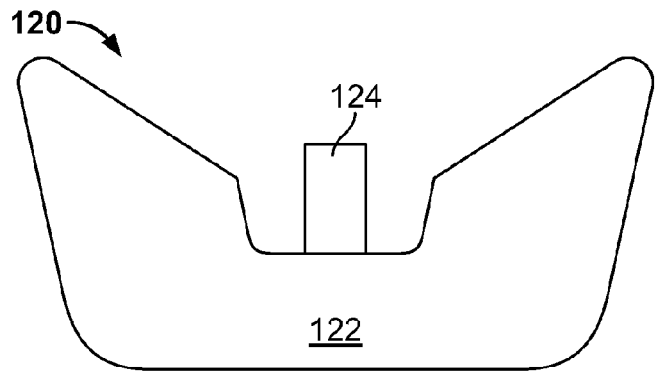
FIG. 12 is a top view of an alternative fusion block for use in conjunction with implants according to the present disclosure.

An alternative fusion block 120 is shown in FIG. 12. Fusion block 120 is composed of a non-circular columnar body 122 that defines a profile a connector stem 124 that extends from the columnar body 122. The profile of this alternative fusion block 120 provides for a single block to cooperate with both anterolateral edges 36a, 36b in contrast to the two fusion blocks 16, 18 described previously. The connector stem 124 is adapted to be received by and mate with insertion hole 58 or 76 of the first or second inter-vertebral element 12, 14, respectively. The block height would be generally be comparable to height "L" shown with respect to fusion block 16 in FIG. 10, substantially matching the height "H" of the assembled disc implant 10.

Thus, as described herein, the fusion block(s) 16, 18, 120 may be attached to the first or the second inter-vertebral element 12, 14. Alternatively, fusion block(s) 16, 18, 120 may be mounted with respect to the first and second inter-vertebral elements 12, 14 by positioning at least a portion of connector stem 112, 124 between the first and second inter-vertebral elements 12, 14. In addition, the disclosed fusion blocks 16, 18, 120 may be provided without a connector stem and may be associated with the first and second inter-vertebral elements 12, 14 by anterior positioning relative to the first and second inter-vertebral elements 12, 14 in a non-secured fashion.

An exemplary alternative to the described fusion blocks involves use of a malleable bone graft material and placement of such graft material anterior to the disc implant. Malleable bone graft material is well established in the art, and can be composed of materials described in the coating section, as well as bone (xenograft, allograft, autograft), bone products (such as demineralized bone matrix) and polymers, and combinations of these materials.

4. Two Piece Artificial Disc

Figure 13:
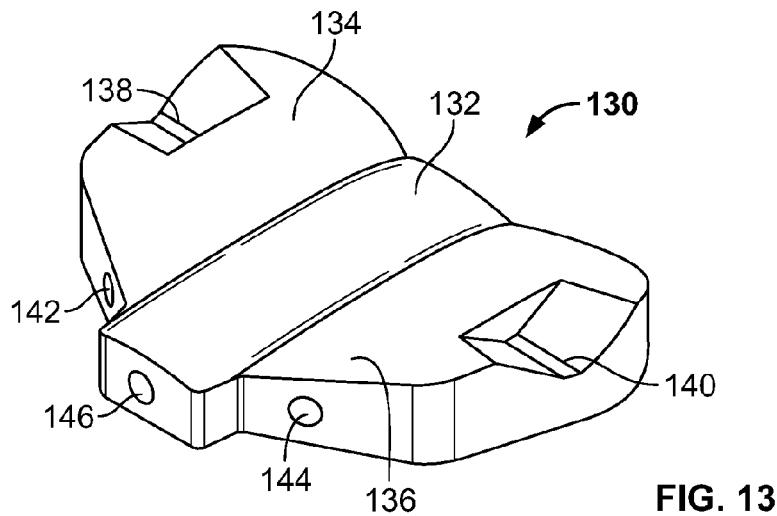
FIG. 13 is an oblique view of an alternative component/intervertebral element of a further implant according to the present disclosure.
Figure 14:
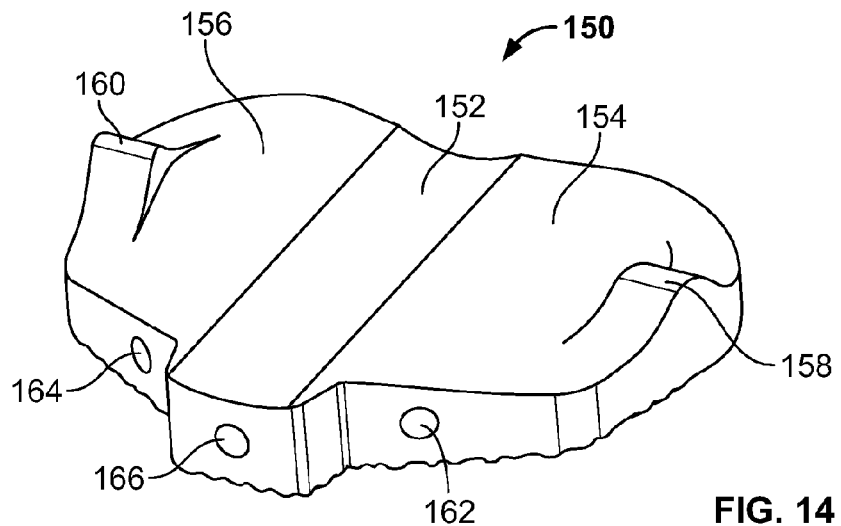
FIG. 14 is an oblique view of an alternative second component/intervertebral element for use with the component/intervertebral element depicted in FIG. 13, showing the face/geometry that would facing the component/intervertebral element of FIG. 13.

FIG. 13 shows an oblique view of an alternative first inter-vertebral element 130 according to an exemplary two piece artificial disc according to the present disclosure. The first inter-vertebral element 130 includes a central region 132, two wings 134, 136 that extend from the central region 132, slots 138, 140 formed in the periphery of wings 134, 136, respectively, and insertion holes 142, 144, 146. FIG. 14 shows an oblique view of an alternative second inter-vertebral element 150 of the disclosed two piece artificial disc. The second inter-vertebral element 150 includes a central region 152, two wings 154, 156 that extend from the central region 152, two upstanding bosses 158, 160 on the periphery of wings 154, 156, respectively, and insertion holes 162, 164, 166. Generally, the central region 132 of the first inter-vertebral element 130—which is in engaging contact with the central region 152 of the second inter-vertebral element 150—provides the primary region of contact between the first and second inter-vertebral elements 130, 150, and such engaging conduct defines an articulating region therebetween. One or more polymeric elements may be positioned between the first and second inter-vertebral elements 130, 150 to reduce and/or eliminate metal-to-metal contact therebetween.

Generally, the articulating region defined between the opposing central regions 132, 152 provides primary contact between the first or second inter-vertebral element 130, 150 of the disclosed two piece artificial disc. The wings 134, 136 provide limits to lateral bending via mating geometry on the second inter-vertebral element 150. Further, the wings 134, 136 contain the slots 138, 140 which, in concert with the bosses 158, 160 of the second inter-vertebral element 150, resist or limit anterior-posterior translation of either the first or second inter-vertebral elements 130, 150 with respect to the other, as well as to resist or limit axial rotation of either the first or second inter-vertebral elements 130, 150 with respect to the other. Similarly, the wings 154, 156 provide limits to lateral bending via mating geometry on the first inter-vertebral element 130. Further, the wings 154, 156 have the bosses 158, 160 which, in concert with the slots 138, 140 of the first inter-vertebral element 130, serve to resist or limit anterior-posterior translation of either the first or second inter-vertebral element 130, 150 with respect to the other, as well as to resist or limit axial rotation of either the first or second inter-vertebral element 130, 150 with respect to the other. Of note, the disclosed inter-vertebral elements 130, 150 are generally symmetric about an anterior-posterior plane passing through the central insertion hole 146, 166.

The first and second inter-vertebral elements 130, 150 do not include openings in their respective wings to facilitate bone in-growth. However, in all other material respects, first and second inter-vertebral elements 130, 150 are completely analogous to the first and second inter-vertebral elements 12, 14 described above. Accordingly, reference is made to the prior discussion of first and second inter-vertebral elements 12, 14 for a complete understanding of the features, functions and benefits of a two-piece disc implant incorporating first and second inter-vertebral elements 130, 150, as described herein.

5. Bone Preparation Instruments and Associated Implant

It is well accepted that it is important to ensure the stability of an implant in the disc space and especially important that the implant resist anterior motion relative to the bone (so-called anterior subluxation or anterior migration). The roughened surfaces described earlier are means to prevent anterior motion from occurring.

An alternative way of preventing anterior motion from occurring is to machine a feature into the bone (the negative) and then have an implant with a matching feature to fit (the positive). FIGS. 15 through 19 show exemplary instruments and implants to achieve such "keyed" implantation.

Figure 15:
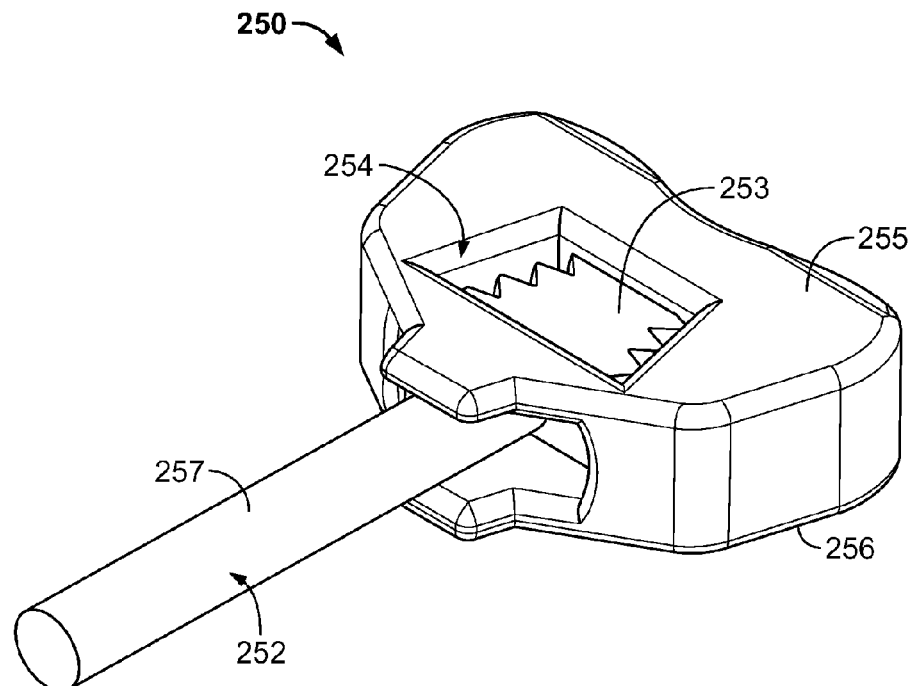
FIG. 15 is an oblique view of an assembly of an exemplary trial implant and bone cutting instrument according to the present disclosure, with the cutting instrument in a non-cutting position.
Figure 16:
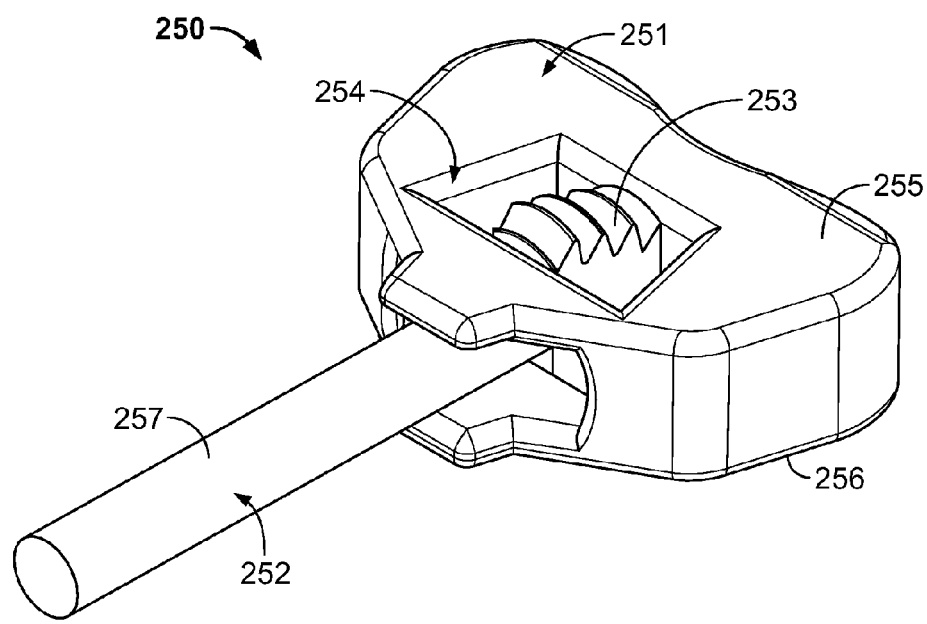
FIG. 16 is an oblique view of the assembly of a trial implant and bone cutting instrument according to FIG. 15, with the cutting instrument in a cutting position.
Figure 17:
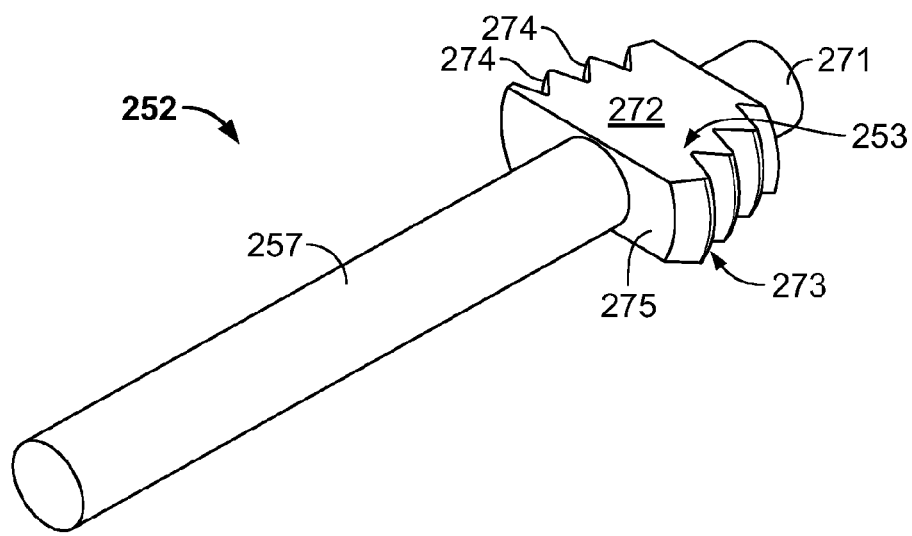
FIG. 17 is an oblique view of the exemplary bone cutting instrument associated with the assembly of FIGS. 15 and 16.
Figure 18:
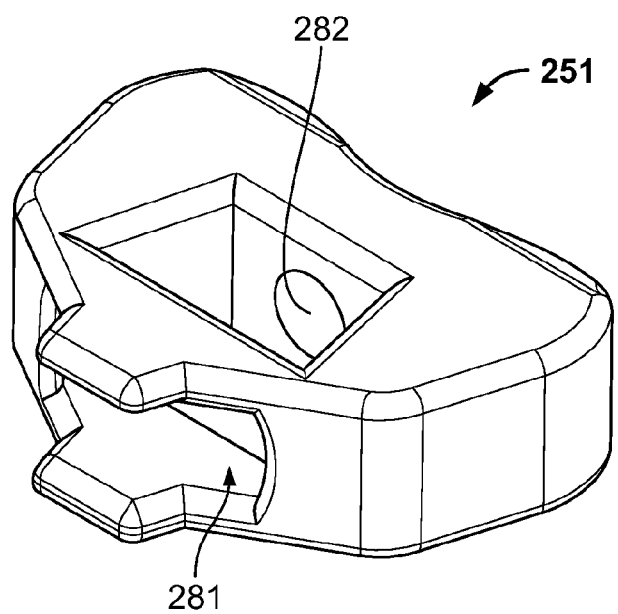
FIG. 18 is an oblique view of a trial implant associated with the assembly of FIGS. 15 and 16.

FIGS. 15 and 16 show an assembly 250 of a trial implant 251 with a bone cutting instrument 252. The trial implant 251 allows a surgeon to assess the disc space and particularly to consider the appropriate size (including potentially footprint, height and lordosis) for an implant. The bone cutting instrument 252 is used in conjunction with a trial implant 251 to selectively remove bone from adjacent vertebral bodies, thereby creating a feature in the bone (the negative) to accommodate an implant. The cutting portion 253 of the bone cutting instrument 252 is within a pocket 254 defined in the trial implant 251.

As further shown in FIGS. 15 and 16, the bone cutting instrument 251 has at least two types of positions. The first type of position, exemplified in FIG. 15, positions the bone cutting portion 253 to be between the top surface 255 and the bottom surface 256 of the trial implant 251. This first position allows the assembled cutting instrument 253 and trial implant 251 to be passed into the surgical site while minimizing potential risk to adjacent tissues, such as vessels (the "safe positions"). In FIG. 16, a second type of position is shown wherein the bone cutting portion 253 is outside of both the top surface 255 and the bottom surface 256 (the "cutting positions"). As shown, the bone cutting instrument 253 is moved between the two types of positions via rotations about the shaft 257 of the instrument. When the bone cutting instrument is rotated completely about its shaft 257 while in the trial implant 251, it machines a cavity in the bone adjacent to the trial implant 251.

The bone cutting instrument geometry enables the two positions shown in FIGS. 15 and 16. As shown in the disassembled view of FIG. 17, the bone cutting instrument 252 has a bone cutting portion 253, a shaft 257, a boss 271 and abutting faces 272 and 273 on the bone cutting portion. When the distance between the abutting faces is equal to or less than the distance between the top surface 255 and the bottom surface 256 of the trial implant 251 (i.e., the height of the trial implant), then the bone cutting instrument 252 may be rotated to one or more "safe positions". Alternatively, for the bone cutting instrument 252 to be capable of cutting bone, the distance from the axis of the shaft 257 to the peak of the cutting teeth 274 must exceed the height of the trial implant 251. This allows the bone cutting instrument 252 to engage tissue adjacent to the top surface 255 and bottom surface 256 of the trial implant 251.

In exemplary embodiments, the bone cutting instrument 252 simultaneously creates a cavity in both the bone above the trial implant 251 as well as the bone below the trial implant 251, by virtue of the location of the central slot 281 and hole 282 receiving the bone cutting instrument 252 generally (see FIG. 18) and the boss 271 of the bone cutting instrument 252 that mates with the hole 282.

Alternatively, the trial implant 251 could accommodate two holes 282 to receive the bone cutting instrument 252, with both holes an equal distance from the nearest face (i.e., top surface 255 and bottom surface 256). In this alternative embodiment, the bone cutting instrument 252 could be assembled into one hole 282, rotated to create a bone cavity on one side of the trial implant 251, then assembled into the second hole and rotated to create a bone cavity on the other side of the trial implant 251.

According to exemplary embodiments of the present disclosure, bone material generated through creation of the bone cavity, e.g., using the disclosed bone cutting instrument 252, may be captured for subsequent use. For example, bone material may be used for analytical purposes, e.g., biopsy, and/or to promote bone growth/bone grafting. Devices for use in capturing such bone material are known in the art and may be used in conjunction with bone cutting instrument 252 to capture bone shavings, bone chips and the like.

Figure 21:
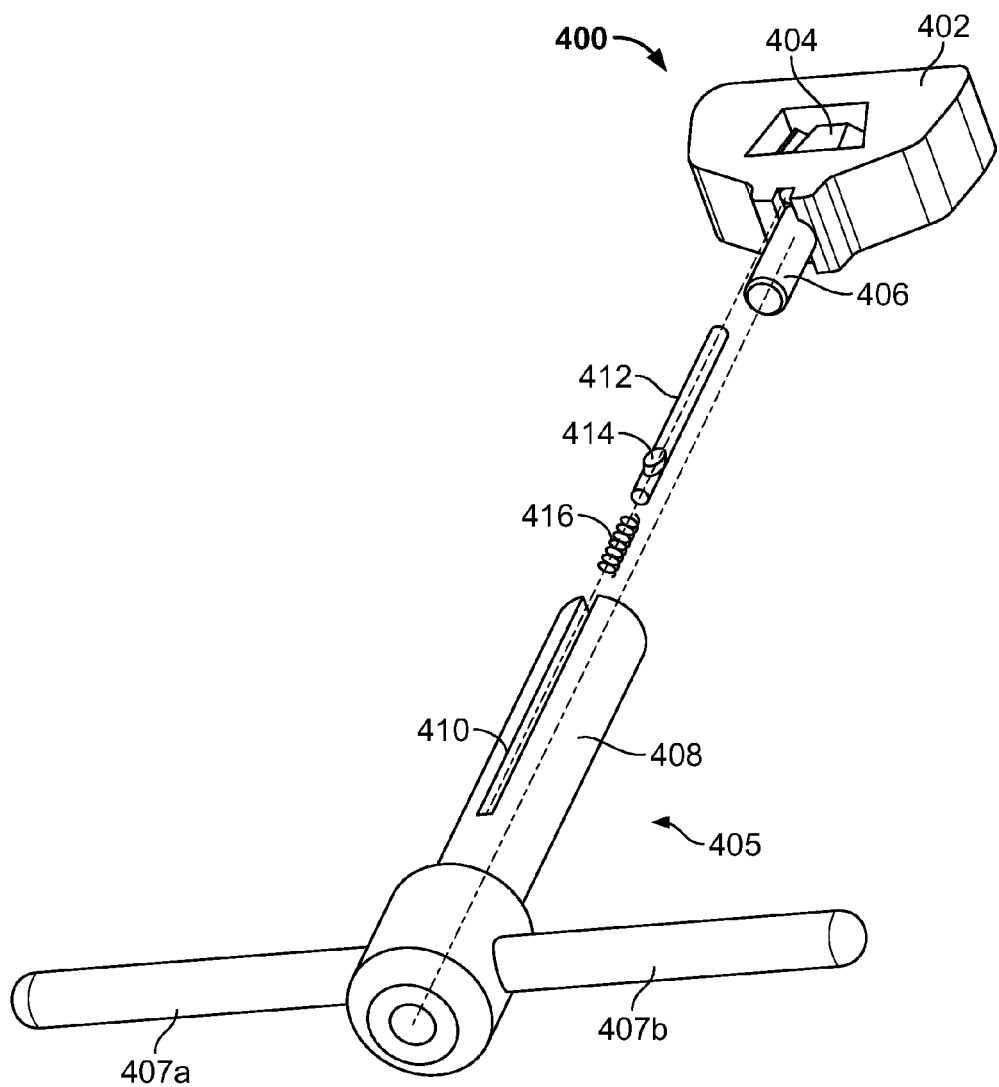
FIG. 21 is a partially exploded view of an alternative exemplary trial implant and bone cutting instrument, with the cutting instrument in a non-cutting position.

With reference to FIG. 21, a partially exploded view of a further exemplary bone cutting device 400 is provided according to the present disclosure. Bone cutting device 400 includes a trial implant 402 that is structurally corresponds to trial implant 251 described above. Trial implant 402 accommodates bone cutting instrument 404, which is shown in a non-cutting orientation in FIG. 21. Bone cutting instrument 404 includes an outwardly extending shaft 406 that facilitates reorientation of the bone cutting instrument 404 between cutting and non-cutting orientations. A handle member 405 is adapted to detachably engage shaft 406. Handle member 405 includes first and second handle extensions 407a, 407b that facilitate user interaction therewith.

Handle member 405 also defines a substantially cylindrical extension 408 that defines an axial slot 410. A sliding pin 412 is sized for cooperation with cylindrical extension 408. Sliding pin 412 defines a transversely extending button 414 that is sized so as to ride above slot 410 with sliding pin 412 positioned within cylindrical extension 408. A compression spring 416 is positioned within cylindrical extension 408 and engages the proximal end of sliding pin 412. Compression spring 416 biases sliding pin 412 relative to handle member 405.

In use, the distal end of sliding pin 412 may be brought into alignment with a corresponding aperture associated with bone cutting instrument 404 while the distal end of cylindrical extension 408 is aligned with and substantially surrounds shaft 406. Once sliding pin 412 is engaged with bone cutting instrument 404, bone cutting instrument 404 is prevented from rotational motion. Thus, until released, the sliding pin 412 locks the bone cutting instrument in a non-cutting orientation. The sliding pin 412 may be disengaged from the bone cutting instrument 404 by retraction thereof in a proximal direction, i.e., against the bias of compression spring 416. In this way, the bone cutting instrument 404 may be freed for movement into a cutting orientation.

Figure 19:
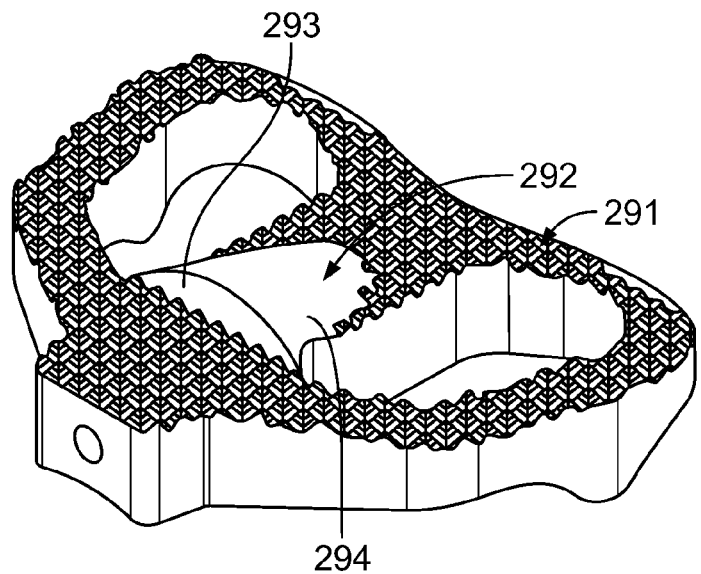
FIG. 19 is an oblique view of an exemplary implant that is configured and dimensioned to mate with the space created by a bone cutting instrument according to the present disclosure.

An exemplary inter-vertebral element 291 associated with a disc implant according to the present disclosure is depicted in FIG. 19. The disclosed inter-vertebral element includes a matching feature that is configured and dimensioned to cooperate with a cavity formed in bone. Inter-vertebral element 291 thus includes feature 292 to mate with a bone cavity created by the bone cutting instrument 252. The feature 292 has a face 293 and a tapered lead in 294. The face 293 is adapted to mate with the trailing face 275 of the bone cutting instrument 252 to provide a way to resist motion of the inter-vertebral element 291 relative to the adjacent bone. The tapered lead 294 permits relatively easy insertion of the implant into the disc space. Of note, the orientation of feature 292 would be adjusted to accommodate side placement of the disclosed implant, as will be apparent to persons skilled in the art.

As shown, the cutting surface of the bone cutting instrument 252 is tapered to match the tapered lead 294 of the implant. Other geometries for these mating geometries can also be considered.

6. Center of Rotation

The implants of the present disclosure—whether utilized as a fusion device or an artificial disc—advantageously provide in situ variability as to the center of rotation defined by the implant. By in situ variability is meant that the first and second inter-vertebral elements are coupled such that the center of rotation defined thereby can be defined at various positions—within certain boundaries—based on in situ interaction between such inter-vertebral elements and surrounding anatomical structures/features. In exemplary embodiments of the present disclosure, the first and second inter-vertebral elements are coupled so as to accommodate relative motion—within certain boundaries—in all directions, i.e., full range freedom-of-motion. In fusion implant implementations of the present disclosure, the noted full range freedom of motion exists at the time of implantation and for a period of time thereafter. However, as bone in-growth advances, the degree to which the first and second inter-vertebral elements are free to move relative to each other is gradually reduced until a fused state is achieved. Once in a fused state, the first and second inter-vertebral elements are no longer free to move relative to each other in any direction, i.e., the first and second inter-vertebral elements are fixed relative to each other. In alternative implementations of the present disclosure, e.g., artificial disc implementations, the noted freedom of motion in all directions—within certain boundaries—may be maintained indefinitely post-implantation.

Figure 20:
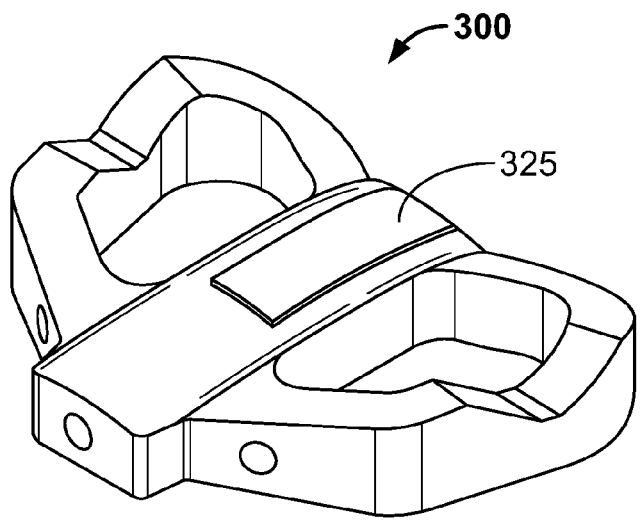
FIG. 20 is an isometric view of an exemplary implant according to the present disclosure that schematically depicts an exemplary contact point/region.

With reference to FIG. 20, an exemplary inter-vertebral element 300 according to the present disclosure is schematically depicted. As is readily apparent, inter-vertebral element 300 is adapted to cooperate with a second inter-vertebral element (not pictured) to form a complete implant according to the present disclosure. FIG. 20 depicts only a single inter-vertebral element 300 for clarity purposes. Of note, inter-vertebral element 300 corresponds in structural respects with inter-vertebral element 12 of FIG. 3, so a detailed discussion of such structural features and related functional operations of inter-vertebral element 300 are omitted herein, reference being made to the previous discussion with respect to inter-vertebral element 12 (and complementary inter-vertebral element 14), including specifically the discussion of implant 10 and FIGS. 1-8.

Exemplary inter-vertebral element 300 is adapted to be movably coupled relative to a second/complementary inter-vertebral element (not pictured) in the manner described with reference to inter-vertebral elements 12, 14 of implant 10 (see FIGS. 1-8). Thus, the exemplary coupling mechanism of implant 10 may be utilized with respect to inter-vertebral element 300 so as to permit inter-vertebral element 300 and a second/complementary inter-vertebral element (not pictured) to reposition themselves relative to each other, within certain boundaries. The boundaries are established by the nature of the coupling therebetween. Thus, within boundaries, relative motion between the two inter-vertebral elements is permitted in three rotations (flexion/extension, lateral bending, axial rotation) as well as two translations (anterior-posterior, medial lateral). Translations in the superior-inferior direction are coupled based on displacements in the other directions. Different geometries associated with the elements provide constraints to relative motion between the elements.

For example, with reference to the exemplary first and second inter-vertebral elements 12, 14 of FIGS. 1-8, translational anterior-posterior motion is limited by the interaction between the disclosed bosses/slots. In like measure, translational side-to-side motion is limited by the interaction between the opposed central regions 44, 62. Still further, relative rotational motion—which generally takes the form of a rocking/pivoting motion relative to central regions 44, 62—is limited by the structural engagements between the first and second inter-vertebral elements. However, within the noted boundaries, relative motion between the first and second inter-vertebral elements is permitted—at least for an initial post-implantation period. As the two elements move relative to each other, the contact point/region between them may change—and, with such motion, the center of rotation of the disclosed implant, e.g., implant 10, moves relative to the first and second inter-vertebral elements.

As schematically depicted in FIG. 20, the contact point/region of inter-vertebral element 300 relative to a second/complementary inter-vertebral element (not pictured) is free to move within a region 325. Of note, region 325 is not a "physical" region having demarcation on or with respect to inter-vertebral element 300. Rather, region 325 as schematically depicted in FIG. 20 is merely for illustration purposes. The overall dimensions of contact point/region 325 are generally defined by the coupling mechanisms associated with the disclosed implant. Thus, greater relative movement between the first and second inter-vertebral elements may be accommodated—thereby enlarging the contact point/region 325 in one or more directions—by incorporating coupling mechanism(s) that permit greater translational and/or rotational/pivotal motion as between the first and second inter-vertebral elements. Conversely, a contact point/region 325 of smaller dimension may be achieved by further limiting the range of relative motion between the first and second inter-vertebral elements, e.g., by incorporating coupling mechanisms that limit translational and/or rotational/pivotal motion as between the first and second inter-vertebral elements.

By providing an implant that accommodates automatic repositioning of the contact point/region, and therefore the center of rotation post-implantation, the present disclosure greatly improves the clinical performance of the disclosed implants. More particularly, automatic repositioning of the center of rotation of the disclosed implant, e.g., based on load and motion factors associated with a specific patient, permits the implant to better respond to spinal requirements and reduces unbalanced and/or shear forces associated with in situ operation of the disclosed implant.

Although the present disclosure has been described with reference to exemplary implementations thereof, the present disclosure is not limited by or to such exemplary implementations. Rather, the disclosed spine implants and instrumentation are susceptible to various modifications, refinements and/or enhancements as will be readily apparent to persons skilled in the art, such modifications, refinements and enhancements being expressly encompassed within the scope of the present disclosure.

The invention claimed is:

1. A disc implant, comprising:
   a first inter-vertebral element defining a first inner face that includes a first central region and the first inter-vertebral element defining a first outer face; and
   a second inter-vertebral element defining a second inner face that includes a second central region and the second inter-vertebral element defining a second outer face;
   wherein the first and second inner faces of the first and second inter-vertebral elements are adapted to be positioned in a facing alignment;
   wherein the first and second outer faces of the first and second inter-vertebral elements are adapted to be positioned facing away from each other and configured to be placed adjacent to respective vertebra of a vertebral column of a patient;
   wherein the first central region defines a first profile configured to be placed in a medial-lateral direction relative to the vertebral column of the patient that is defined by a single arc and a second profile configured to be placed in an anterior-posterior direction relative to the vertebral column of the patient that (i) extends from an anterior edge of the first central region to a posterior edge of the first central region, and (ii) is defined by at least two arcs; and
   wherein the second central region defines a first profile configured to be placed in a medial-lateral direction relative to the vertebral column of the patient that is defined by a single arc and a second profile configured to be placed in an anterior-posterior direction relative to the vertebral column of the patient that (i) extends from an anterior edge of the second central region to a posterior edge of the second central region, and (ii) is defined by a linear line.

2. The disc implant according to claim 1, wherein at least one of the medial-lateral and anterior-posterior profiles of the first and second inter-vertebral elements are substantially the same in at least one direction.

3. The disc implant according to claim 1, wherein the first and second inter-vertebral elements include one or more structural features that resist, but do not prevent, axial rotation and anterior-posterior translation of the first and second inter-vertebral elements relative to each other.

4. The disc implant according to claim 1, wherein the first and second inter-vertebral elements include one or more structural features that limit lateral bending of the first and second inter-vertebral elements relative to each other.

5. The disc implant according to claim 1, wherein the first and second inter-vertebral elements each define a first wing that extends laterally relative to the first and second central regions in a first direction, and a second wing that extends laterally in a second direction relative to the first and second central regions.

6. The disc implant according to claim 5, wherein the first central region of the first inter-vertebral element and the second central region of the second inter-vertebral element are adapted to be placed in abutting relation, and wherein abutting engagement of such first and second central regions establishes at least in part an articulating geometry thereof.

7. The disc implant according to claim 5, wherein cooperative structures are defined on the respective first and second wings of the first and second inter-vertebral elements that accommodate relative motion between the first and second inter-vertebral elements.

8. The disc implant according to claim 7, wherein the cooperative structures include upstanding bosses and slots.

9. The disc implant according to claim 8, wherein each cooperative upstanding boss and slot define an anterior gap, a posterior gap and a distal gap.

10. The disc implant according to claim 5, wherein the first and second wings define openings that accommodate bone in-growth.

11. The disc implant according to claim 1, wherein the first and second inter-vertebral elements are movably coupled relative to each other, and wherein the first and second inter-vertebral elements become fixed or fused relative to each other after a period of time post-implantation.

12. The disc implant according to claim 11, wherein the first and second inter-vertebral elements become fixed or fused due to bone in-growth.

13. The disc implant according to claim 1, wherein at least one of the first outer face and the second outer face of the first and second inter-vertebral elements includes surface features that promote fixation relative to adjacent anatomical structures.

14. The disc implant according to claim 1, wherein the disc implant functions in situ as at least one of a fusion device and an artificial disc.

15. The disc implant according to claim 1, wherein the first and second inter-vertebral elements are movably coupled so as to define a contact point or a contact region between the first and second inter-vertebral elements that is moveable post-implantation.

16. The disc implant according to claim 15, wherein the contact point or the contact region is moveable within a zone or a region in both the anterior-posterior direction as well as the medial-lateral direction.

17. The disc implant according to claim 1, further comprising a polymeric member positioned between the first and second inter-vertebral elements.

18. The disc implant according to claim 1, wherein the second profile of the second central region extends from an anterior edge of the second central region to a posterior edge of the second central region.

19. In combination:
    (a) a disc implant adapted to be positioned between two vertebrae of a vertebral column of a patient, the disc implant comprising:
        (i) a first inter-vertebral element defining a first inner face that includes a first central region and the first inter-vertebral element defining a first outer face; and
        (ii) a second inter-vertebral element defining a second inner face that includes a second central region and the second inter-vertebral element defining a second outer face;
    wherein the first and second inner faces of the first and second inter-vertebral elements are adapted to be positioned in a facing alignment;
    wherein the first and second outer faces of the first and second inter-vertebral elements are adapted to be positioned facing away from each other and configured to be placed adjacent to respective vertebra of the vertebral column of the patient;
    wherein the first central region defines a first profile configured to be placed in a medial-lateral direction relative to the vertebral column of the patient that is defined by a single arc and a second profile configured to be placed in an anterior-posterior direction relative to the vertebral column of the patient that (i) extends from an anterior edge of the first central region to a posterior edge of the first central region, and (ii) is defined by at least two arcs; and
    wherein the second central region defines a first profile configured to be placed in a medial-lateral direction relative to the vertebral column of the patient that is defined by a single arc and a second profile configured to be placed in an anterior-posterior direction relative to the vertebral column of the patient that (i) extends from an anterior edge of the second central region to a posterior edge of the second central region, and (ii) is defined by a linear line; and
    (b) a posterior stabilization device, wherein the posterior stabilization device provides support to at least one of the disc implant and the two vertebrae.

20. The combination of claim 19, wherein the posterior stabilization device is selected from the group consisting of a flexible implant, a dynamic implant, a semi-rigid implant and a rigid implant.

* * * * *